(12) United States Patent
Dahlberg et al.

(10) Patent No.: US 7,005,285 B1
(45) Date of Patent: Feb. 28, 2006

(54) HUMAN P21-ACTIVATED KINASE 5 POLYPEPTIDE

(75) Inventors: Mats Dahlberg, Stockholm (SE); Jurgen Moll, Appiano Gentile (IT); Arturo Galvani, Parabiago (IT)

(73) Assignee: Pharmacia & Italia S.P.A., Milano (IT)

( * ) Notice: Subject to any disclaimer, the term of this patent is extended or adjusted under 35 U.S.C. 154(b) by 0 days.

(21) Appl. No.: 10/130,323

(22) PCT Filed: Nov. 14, 2000

(86) PCT No.: PCT/EP00/10736

§ 371 (c)(1),
(2), (4) Date: Sep. 3, 2002

(87) PCT Pub. No.: WO01/36602

PCT Pub. Date: May 25, 2001

Related U.S. Application Data

(63) Continuation-in-part of application No. 09/439,756, filed on Nov. 15, 1999, now abandoned.

(51) Int. Cl.
*C12N 9/12* (2006.01)
(52) U.S. Cl. ................................................ 435/194
(58) Field of Classification Search ................ 435/194; 424/94.5; 514/2
See application file for complete search history.

(56) References Cited

U.S. PATENT DOCUMENTS 6,013,500 A    1/2000   Minden ...................... 435/194

FOREIGN PATENT DOCUMENTS

WO    WO 99/53036    10/1999
WO    WO 00/58473    10/2000

OTHER PUBLICATIONS

Branden et al. "Introduction to Protein Structure", Garland Publishing Inc., New York, 1991.*
Witkowski et al. (1999)Biochemistry 38:11643-11650.*
GenBank Accession No. AB033090, Nov. 11, 1999.*
New England Biolabs 1996/97 Catalog, p. 147.*
Abo, A. et al., "PAK4, a novel effector for Cdc42Hs, is implicated in the reorganization of the actin cytoskeleton and in the formation of filopodia", *EMBO Journal*, 1998, 17(22), 6527-6540.
Bagrodia, S. et al., "PAK to the Future", *Trends in Cell Biology*, 1999, 9, 350-355.
Bagrodia, S. et al., "A Tyrosine-phosphorylated Protein That Binds to an Important Regulatory Region on the Cool Family of p21-activated Kinase-binding Proteins", *J. Biol. Chem.*, 1999, 274(32), 22393-400.

Bagrodia, S. et al., "A Novel Regulator of p21-activated Kinases", *J. Biol. Chem.*, 1998, 273(37), 23633-23636.
Bokoch, G.M. et al., "Interaction of the Nck Adapter Protein with p21-activated Kinase (PAK1)",*J. Biol. Chem.*, 1996, 271(42), 25746-25749.
Bokoch, G.M. et al., "A GTPase-independent Mechanism of p21-activated Kinase Activation", *J. Biol. Chem.*, 1998, 273(14), 8137-8144.
Burbelo, P.D. et al., "A Conserved Binding Motif Defines Numerous Candidate Target Proteins for Both Cdc42 and Rac GTPases",*J. Biol. Chem.*, 1995, 270(49), 29071-29074.
Hanks, S.K. et al., "Protein Kinase Catalytic Domain Sequence Database: Identification of Conserved Features of Primary Structure and Classification of Family Members", *Methods in Enzymology*, 1991, 200, 38-62.
Lian, J.P. et al., "Products of Sphingolipid Catabolism Block Activation of the p21-Activated Protein Kinases in Neutrophils", *J. Immunol.*, 1998, 161, 4375-4381.
Manser, E. et al., "PAK Kinases Are Directly Coupled to the PIX Family of Nucleotide Exchange Factors" *Molecular Cell.*, 1998, 1, 183-192.
Nagase, T. et al., "Prediction of the Coding Sequences of Unidentified Human Genes. XV. The Complete Sequences of 100 New cDNA Clones From Brain which Code for Large Proteins in Vitro", *DNA Research*, 1999, 6(5), 337-345.
Tang, Y. et al., "A role for Pak protein kinases in Schwann cell transformation", *Proc. Natl. Acad. Sci USA*, 1998, 95, 5139-5144.
Watanabe, N.M. et al., "PAK5, A Novel Group II Pak Family Kinase that id Predominately Expressed in Brain", 2000, XP002164869, pp. 1-2.
Yablonski, D. et al., "A Nck-Pak1 signaling module is required for T-cell receptor-mediated activation of NFAT, but not of JNK", *EMBO J.*, 1998, 17(19), 5647-5657.
Bridgeman, A. "Human DNA Sequence from Clone RP5-1119D9 on Chromosome 20p12", *Direct Submission*, Dec. 1, 2000, GenBank ACCESSION # AL 031652.
Melzig, J. et al., "A protein related to p21-activated kinase (PAK) that is involved in neurogenesis in the *Drosophila* adult central nervous system", *Current Biology*, 1998, 8, 1223-1226.
Ohara, O. et al., "Construction and Characterization of Human Brain cDNA Libraries Suitable for Analysis of cDNA Clones Encoding Relatively Large Proteins", *DNA Research*, 1997, 4, 53-59.

* cited by examiner

*Primary Examiner*—David J. Steadman
(74) *Attorney, Agent, or Firm*—Steve T. Zelson; E. Victor Donahue

(57) ABSTRACT

The present invention provides a human polypeptide homolog of P21-activated kinase (PAK) polynucleotides which identify and encode PAK5 serine/threonine kinase. In addition, the invention provides expression vectors, host cells and methods for its production. The invention also provides methods for the identification of PAK5 agonists/antagonists, useful for the treatment of human diseases and conditions.

1 Claim, 2 Drawing Sheets

HUMAN P21-ACTIVATED KINASE 5 POLYPEPTIDE

CROSS REFERENCE TO RELATED APPLICATIONS

This application is the National Stage of International Application No. PCT/EP00/10736, filed Nov. 14, 2000, which is a continuation-in-part application of U.S. Application Ser. No. 09/439,756, filed Nov. 15, 1999, now abandoned.

FIELD OF THE INVENTION

The present invention is directed, in part, to nucleic acid molecules encoding p21-activated kinase 5, novel polypeptides, and assays for screening comounds which bind to p21-activated kinase 5 and/or modulate the activity of p21-activated kinase-5.

BACKGROUND OF THE INVENTION

The p-21-activated kinase (PAK) family of serine-threonine kinases (reviewed by Bagrodia and Cerione, Trends in Cell Biology, vol. 9, pp. 350–355, 1999, and references contained therein) currently consists of four members, PAK1 (also known as PAKα), PAK2 (also known as PAKγ), PAK3 (also known as PAKβ), and PAK4. The kinase activity of PAKs is stimulated by binding to the GTP-bound forms of Cdc42 and p21Rac (hereafter referred to as Rac). The C-terminal region of PAK proteins contains the kinase catalytic domain, which shows the highest conservation of sequence homology between different members of the family. The N-terminal region contains a conserved motif thought to be responsible for binding to Cdc42 and Rac GTPases (the 'GBD/CRIB' motif, Burbelo et al., Journal of Biological Chemistry vol. 270, pp. 29071–29074, 1995). PAKs also contain in their N-terminal domains several copies of the PXXP protein motif that represents a binding site for SH3 protein domains. It has been shown that PAKs1–3 posses an N-terminal regulatory region (overlapping with the Cdc42/Rac binding domain) that is responsible for maintaining the kinase in a catalyically inactive form. PAK proteins have recently been shown to utilize sequences within the N-terminal domain for high-affinity binding to two SH3 domain-containing proteins, p85Cool-1/βPix and αPIX/Cool-2 (Manser et al., Mol. Cell vol. 1 pp.183–192, 1998, and Bagrodia et al., J. Biol. Chem. Vol 273, pp. 23633–23636, 1998). p85Cool-1/βPix localizes to peripheral focal complexes, and was found to recruit PAK1 from the cytoplasm to these complexes, while an alternatively spliced version of p85Cool-1/βPIX, p50Cool-1, appears to bind PAK3 and inhibits its kinase activity. Cool-2/αPIX stimulates PAK activity through an as yet unclear mechanism. Two tyrosine phosphorylated proteins, termed Cat-1 and Cat-2 (Cool-associated tyrosine phosphorylated proteins 1 and 2, Bagrodia et al., J Biol Chem vol. 274 pp. 22393–400, 1999) have recently been found to interact with p85Cool-1/βPIX and Cool-2/αPIX, but not with p50Cool-1. It therefore appears likely that Cat-1 and Cat-2 play crucial roles in PAK regulation, since they only interact with forms of Cool/Pix that promote PAK activity.

In addition to these interactions, PAK proteins have been shown to be recruited to activated tyrosine kinase receptors by the SH2/SH3 adapter protein Nck (Bokoch et al., J Biol Chem vol. 271 pp. 25746–9, 1996). This recruitment may provide a link between cell activation by growth factor receptors and PAK signaling pathways. It has also been shown that PAK kinase activity can be stimulated in the absence of Cdc42 or Rac binding by sphingosine and other membrane lipids (Bokoch et al., J Biol Chem vol. 273, pp. 8137–44, 1998), but repressed by products of sphingolipid metabolism (Lian et al., J Immunol vol. 161, pp. 4375–81, 1998).

The downstream consequences of PAK activity are also multifold and complex. PAK proteins have been found to affect assembly of focal contacts, cytosketal organization, neurite outgrowth, lamellipodia formation, membrane ruffling, regulation of cell motility and morphology. PAKs have also been found to activate nuclear mitogen-activated protein kinases (MAPKs), and importantly, to phosphorylate the kinase Raf1, a downstream effector of Ras proteins: in fact, kinase-defective PAK mutants revert the oncogenic activity of mutated Ras (Tang et al., Proc Natl Acad Sci USA vol. 95, pp. 5139–44, 1998). Additionally, PAKs become activated after stimulation of the T-cell receptor, and are required for activation of ERK2 and the NFAT transcription factor, and consequently gene expression by the T-cell receptor (Yablonski et al., EMBO J vol. 17 pp.5647–57, 1998).

In summary, PAK proteins are subject to diverse regulatory inputs, and transmit signals to diverse downstream effectors which are essential for many signaling pathways that are fundamental for cell morphology, motility/migration, proliferation, differentiation or cell death.

The present invention involves the surprising discovery of a novel polypeptide, herein designated p21-activated kinase 5 (henceforth to as "PAK5") and its role as a key component, for example, in regulating cell proliferation, cell migration, cell differentiation, cytoskeletal organisation, gene expression, cell cycle progression, and cell death. PAK5 is, thus, useful in the search for novel agents that can modify and/or control these processes. These and other aspects of the invention are described below.

SUMMARY OF THE INVENTION

The present invention is directed to, in part, isolated nucleic acid molecules comprising SEQ ID NO:1 or a fragment thereof; SEQ ID NO:2, or a fragment thereof; a nucleotide sequence complementary to at least a portion of SEQ ID NO:1 or SEQ ID NO:2; a nucleotide sequence homologous to SEQ ID NO:1 or SEQ ID NO:2 or a fragment thereof; a nucleotide sequence that encodes a polypeptide comprising SEQ ID NO:3 or a fragment thereof; or a nucleotide sequence that encodes a polypeptide comprising an amino acid sequence homologous to SEQ ID NO:3, or a fragment thereof.

The present invention is also directed to recombinant expression vectors comprising any of the nucleic acid molecules described above.

The present invention is also directed to host cells transformed with a recombinant expression vector comprising any of the nucleic acid molecules described above.

The present invention is also directed to methods of producing a polypeptide comprising SEQ ID NO:3, or a homolog or fragment thereof, by introducing a recombinant expression vector comprising any of the nucleic acid molecules described above into a compatible host cell, growing the host cell under conditions suitable for expression of the polypeptide, and recovering the polypeptide from the host cell.

The present invention is also directed to compositions comprising any of the nucleic acid molecules described above and an acceptable carrier or diluent.

The present invention is also directed to isolated polypeptides encoded by any of the nucleic acid molecules described above.

The present invention is also directed to compositions comprising a polypeptide encoded by any of the nucleic acid molecules described above and an acceptable carrier or diluent.

The present invention is also directed to isolated antibodies which bind to an epitope on a polypeptide encoded by any of the nucleic acid molecules described above.

The present invention is also directed to kits comprising antibodies which bind to a polypeptide encoded by any of the nucleic acid molecules described above and a negative control antibody.

The present invention is also directed to methods of inducing an immune response in a mammal against a polypeptide encoded by any of the nucleic acid molecules described above by administering to the mammal an amount of the polypeptide sufficient to induce the immune response.

The present invention is also directed to methods of identifying a compound that binds to PAK5 by contacting PAK5 with a compound, and determining whether the compound binds PAK5.

The present invention is also directed to methods of identifying a compound that binds a nucleic acid molecule encoding PAK5 by contacting PAK5 with a compound, and determining whether the compound binds the nucleic acid molecule.

The present invention is also directed to methods of identifying a compound that modulates the activity of PAK5 by contacting PAK5 with a compound, and determining whether PAK5 activity is modified.

The present invention is also directed to compounds that modulate PAK5 activity identified by contacting PAK5 with the compound, and determining whether the compound modifies activity of PAK5, binds to PAK5, or binds to a nucleic acid molecule encoding PAK5.

These and other aspects of the invention are described in greater detail below.

DETAILED DESCRIPTION OF PREFERRED EMBODIMENTS

The present invention provides, inter alia, isolated and purified polynucleotides that encode PAK5 or a portion thereof, vectors containing these polynucleotides, host cells transformed with these vectors, processes of making PAK5, methods of using the above polynucleotides and vectors, isolated and purified PAK5 and methods of screening compound which modulate PAK5 activity.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "activity" refers to a variety of measurable indicia suggesting or revealing binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event.

as used herein, the "kinase activity" refers to the ability of the protein of the present invention to transfer the γ-phosphate of a purine nucleotide triphosphate to the hydroxyl groups of protein substrates.

As used herein, the abbreviations in lower case, pak5, refer to a gene, cDNA, RNA or nucleic acid sequence while the upper case version, PAK5, refers to a protein, polypeptide, peptide, oligopeptide, or amino acid sequence.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecule, peptide, protein, sugar, nucleotide, or nucleic acid, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the PAK5 or a fragment thereof.

As used herein, the phrase "homologous nucleotide sequence," or "homologous amino acid sequence," or variations thereof, refers to sequences characterized by a homology, at the nucleotide level or amino acid level, of at least about 60%, more preferably at least about 70%, more preferably at least about 80%, more preferably at least about 90%, and most preferably at least about 95% to the entire SEQ ID NO:1 or SEQ ID NO:2, or to at least a portion of SEQ ID NO:1 or SEQ ID NO:2 which encodes a functional domain of the encoded polypeptide, or to SEQ ID NO:3. Homologous nucleotide sequences include those sequences coding for isoforms of PAK5 proteins. Such isoforms can be expressed in different tissues of the same organism as a result of, for example, alternative splicing of RNA. Alternatively, isoforms can be encoded by different genes. Homologous nucleotide sequences include nucleotide sequences encoding for PAK5 proteins of species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequences encoding human PAK1 (SEQ ID NO:4), PAK2 (SEQ ID NO:5), PAK3 (SEQ ID NO:6) or PAK4 (SEQ ID NO:7). Homologous amino acid sequences include those amino acid sequences which encode conservative amino acid substitutions in SEQ ID NO:3, as well as polypeptides having PAK5-like kinase activity, or binding activities characteristics of PAK5. Percent homology can be determined by, for example, the Gap program (Wisconsin Sequence Analysis Package, Version 8 for Unix, Genetics Computer Group, University Research Park, Madison, Wis.), using the default settings, which uses the algorithm of Smith and Waterman (*Adv. Appl. Math.*, 1981, 2, 482–489, which is incorporated herein by reference in its entirety). Homology of the present invention to related known molecules is discussed below.

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission or (for amino acids) by three letter codes.

One aspect of the present invention is directed to nucleic acid molecules comprising novel nucleotide sequences encoding PAK5. The nucleic acid molecules are preferably either RNA or DNA, but may contain both RNA and DNA monomers or peptide nucleic acid monomers. The nucleic acid molecule may be single stranded or double stranded. The monomers of the nucleic acid molecules may be linked via conventional phosphodiester bonds or modified bonds, such as, for example, phosphorothioate bonds and the like. In addition, the sugar moieties of the monomers may be modified by, for example, addition of 2' substitutions which help confer nuclease resistance and/or cellular uptake.

In a preferred embodiment of the invention, the nucleic acid molecule comprises SEQ ID NO:1, which is 2511 bases in length and comprises an open reading frame (ORF) of approximately 2157 nucleotides (from about position 352 to about position 2508 within SEQ ID NO:1) which encodes PAK5. Alternatively, the nucleic acid molecule comprises a fragment of SEQ ID NO:1. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 600 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1900 nucleotides, from about 1901 to about 2000 nucleotides, from about 2001 to about 2100 nucleotides, from about 2101 to about 2200 nucleotides, from about 2201 to about 2300 nucleotides, from about 2301 to about 2400 nucleotides, from about 2401 to about 2500 nucleotides, from about 2501 to about 2511, and any combinations thereof. The fragment can be located within any portion of SEQ ID NO:1. The invention therefore provides fragments of PAK5 which comprise at least 14 preferably at least 16, 18, 20, 25, 50, or 75 consecutive nucleotides.

In another preferred embodiment of the invention, the nucleic acid molecule comprises SEQ ID NO:2, which is 2157 bases in length and comprises the ORF (from about position 352 to about position 2508 within SEQ ID NO:1) described above. Alternatively, the nucleic acid molecule comprises a fragment of SEQ ID NO:2. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 600 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1900 nucleotides, from about 1901 to about 2000 nucleotides, from about 2001 to about 2100 nucleotides, from about 2101 to about 2157 nucleotides, and any combinations thereof. The fragment can be located within any portion of SEQ ID NO:2.

In another preferred embodiment of the invention, the nucleic acid molecule comprises a nucleotide sequence complementary to at least a portion of SEQ ID NO:1 or SEQ ID NO:2. Preferably, the nucleic acid molecule comprises a nucleotide sequence complementary to the entire sequence recited in SEQ ID NO:1 or SEQ ID NO:2. Alternatively, the nucleic acid molecule comprises a nucleotide sequence complementary to a portion of SEQ ID NO:1 or SEQ ID NO:2 (i.e. complementary to any of the fragments described above). Nucleotide sequences complementary to at least a portion of SEQ ID NO:1 or SEQ ID NO:2 include, for example, oligonucleotides which hybridize under stringent hybridization conditions to at least a portion of SEQ ID NO:1 or SEQ ID NO:2. Preferred oligonucleotides comprise at least about 10 nucleotides and as many as about 50 nucleotides, preferably about 15 to 30 nucleotides. They are chemically synthesized and can be used as probes, primers, and as antisense agents.

In another preferred embodiment of the invention, the nucleic acid molecule comprises a nucleotide sequence homologous to SEQ ID NO:1 or SEQ ID NO:2. Preferably, the nucleotide sequence is at least about 60% homologous, more preferably at least about 70% homologous, more preferably at least about 80% homologous, more preferably at least about 90% homologous, and most preferably at least about 95% homologous to the entire SEQ ID NO:1 or SEQ ID NO:2. Alternatively, the nucleotide sequence is at least about 60% homologous, more preferably at least about 70% homologous, more preferably at least about 80% homologous, more preferably at least about 90% homologous, and most preferably at least about 95% homologous to a portion of SEQ ID NO:1 or SEQ ID NO:2 which encodes a functional domain of the polypeptide encoded thereby. In addition, a nucleotide sequence homologous to SEQ ID NO:1 or SEQ ID NO:2 also includes a fragment of the nucleotide sequence homologous to SEQ ID NO:1 or SEQ ID NO:2 of the lengths described above.

In another preferred embodiment of the invention, the nucleic acid molecule comprises a nucleotide sequence that encodes a polypeptide comprising SEQ ID NO:3. The nucleic acid molecule preferably comprises SEQ ID NO:2 or comprises SEQ ID NO:2 containing codon substitutions which reflect the degeneracy of the genetic code. As is well known in the art, because of the degeneracy of the genetic code, there are numerous other DNA and RNA molecules that can code for the same polypeptide as that encoded by SEQ ID NO:2. The present invention, therefore, contemplates these other DNA and RNA molecules which, on expression, encode the polypeptide of SEQ ID NO:3. DNA and RNA molecules other than those specifically disclosed herein characterized simply by a change in a codon for a particular amino acid, are within the scope of the present invention.

As is well known in the art, because of the degeneracy of the genetic code, there are numerous other DNA and RNA molecules that can code for the same polypeptide as that encoded by the aforementioned pak5 gene. The present invention, therefore, contemplates those other DNA and RNA molecules which, on expression, encode the polypeptide of SEQ ID NO:3. Having identified the amino acid residue sequence encoded by a PAK5 gene, and with knowledge of all triplet codons for each particular amino acid residue, it is possible to describe all such encoding RNA and DNA sequences. DNA and RNA molecules other than those specifically disclosed herein characterized simply by a change in a codon for a particular amino acid, are within the scope of this invention.

A table of amino acids and their representative abbreviations, symbols and codons is set forth below in the following Table 1.

TABLE 1

| Amino acid | Abbrev. | Symbol | Codon(s) | |
|---|---|---|---|---|
| Alanine | Ala | A | GCA | GCC GCG GCU |
| Cysteine | Cys | C | UGA | UGU |
| Aspartic acid | Asp | D | GAC | GAU |
| Glutamic acid | Glu | E | GAA | GAG |
| Phenylalanine | Phe | F | UUC | UUU |
| Glycine | Gly | G | GGA | GGC GGG GGU |
| Histidine | His | H | CAC | CAU |
| Isoleucine | Ile | I | AUA | AUC AUU |
| Lysine | Lys | K | AAA | AAG |
| Leucine | Leu | L | UUA | UUG CUA CUC CUG CUU |
| Methionine | Met | M | AUG | |
| Asparagine | Asn | N | AAC | AAU |
| Proline | Pro | P | CCA | CCC CCG CCU |
| Glutamine | Gln | Q | CAA | CAG |
| Arginine | Arg | R | AGA | AGG CGA CGC CGG CGU |
| Serine | Ser | S | AGC | AGU UCA UCC UCG UCU |
| Threonine | Thr | T | ACA | ACC ACG ACU |
| Valine | Val | V | GUA | GUC GUG GUU |
| Tryptophan | Trp | W | UGG | |
| Tyrosine | Tyr | Y | UAC | UAU |

As is well known in the art, codons constitute triplet sequences of nucleotides in mRNA molecules and, as such, are characterized by the base uracil (U) in place of base thymidine (T) (which is present in DNA molecules). A simple change in a codon for the same amino acid residue within a polynucleotide will not change the sequence or structure of the encoded polypeptide.

Alternatively, the nucleic acid molecule comprises a nucleotide sequence that encodes a fragment of the polypeptide encoding SEQ ID NO:3. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 719 amino acids, and any combinations thereof. The fragment can be located within any portion of SEQ ID NO:3.

In another preferred embodiment of the invention, the nucleic acid molecule comprises a nucleotide sequence that encodes a polypeptide comprising an amino acid sequence homologous to SEQ ID NO:3. Alternatively, the nucleic acid molecule comprises a nucleotide sequence that encodes a fragment of the polypeptide comprising an amino acid sequence homologous to SEQ ID NO:3. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 719 amino acids, and any combinations thereof. The fragment can be located within any portion of SEQ ID NO:3.

With the knowledge of the nucleotide sequence information disclosed in the present invention, one skilled in the art can identify and obtain nucleotide sequences which encode PAK5 from different sources (i.e., different tissues or different organisms) through a variety of means well known to the skilled artisan and disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, DNA which encodes PAK5 may be obtained by screening of mRNA, cDNA, or genomic DNA with oligonucleotide probes generated from the PAK5 gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the PAK5 nucleotide sequences described above can alternatively be recovered by use of the polymerase chain reaction (PCR) procedure, with the PCR oligonucleotide primers produced from the nucleotide sequences provided herein. See U.S. Pat. Nos. 4,683,195 to Mullis et al. and 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template-dependent, polymerase mediated replication of a desired nucleic acid molecule.

A wide variety of alternative cloning an in vitro amplification methodologies are well known to those skilled in the art. Examples of these techniques are found in, for example, Berger et al., *Guide to Molecular Cloning Techniques*, Methods in Enzymology 152 Academic Press, Inc., San Diego, Calif. (Berger), which is incorporated herein by reference in its entirety.

The nucleic acid molecules of the present invention, and fragments derived therefrom, are useful for screening for restriction fragment length polymorphism (RFLP) associated with certain disorders, as well as for genetic mapping.

Antisense oligonucleotides, or fragments of SEQ ID NO:1 or SEQ ID NO:2, or sequences complementary thereto, derived from the nucleotide sequences of the present invention encoding PAK5 are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of SEQ ID NO:1 or SEQ ID NO:2 or mRNA corresponding thereto, including, but not limited to, the initiation codon, TATA box, enhancer sequences, and the like.

Automated sequencing methods were used to obtain or verify the nucleotide sequence of pak5. The pak5 nucleotide sequences of the present invention were obtained for both DNA strands, and are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Another aspect of the present invention is directed to vectors, or recombinant expression vectors, comprising any of the nucleic acid molecules described above. Vectors are used herein either to amplify DNA or RNA encoding PAK5 and/or to express DNA which encodes PAK5. Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, parvoviruses, herpesviruses, poxviruses, adeno-associated viruses. Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT vectors, pGEM vectors (Promega), pPROEXvectors (LTI, Bethesda, Md.), Bluescript vectors (Stratagene), pQE vectors (Qiagen), pSE420 (Invitrogen), and pYES2 (Invitrogen).

Preferred expression vectors are replicable DNA constructs in which a DNA sequence encoding PAK5 is operably linked to suitable control sequences capable of effecting the expression of the PAK5 in a suitable host. DNA regions are operably linked when they are functionally related to each other. For example, a promoter is operably linked to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences into the expression vector will vary depending upon the host selected and the transformation method chosen. Generally, control sequences include a transcriptional promoter, an optional operator sequence to control transcription, a sequence encoding suitable mRNA ribosomal binding, and sequences which control the termination of transcription and translation.

Preferred vectors preferably contain a promoter which is recognized by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist, et al. *Nature*, 1981, 290, 340–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding PAK5 and result in the expression of the mature PAK5 protein.

Moreover, suitable expression vectors can include an appropriate marker which allows the screening of the transformed host cells. The transformation of the selected host is carried out using any one of the various techniques well known to one of skill in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and pak5 DNA. An example of a suitable marker is dihydrofolate reductase (DHFR) or thymidine kinase (see, U.S. Pat. No. 4,399,216).

Nucleotide sequences encoding PAK5 may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesiderable joining, and ligation with appropriate ligases. Techniques for such manipulation are disclosed by Sambrook et al., supra and are well known in the art. Methods for construction of mammalian expression vectors are disclosed in, for example. Okayama et al., *Mol. Cell. Biol.*, 1983 3, 280, Cosman et al., *Mol. Immunol.*, 1986, 23, 935, Cosman et al., *Nature*, 1984, 312, 768, EP-A-0367566, and WO 91/18982, each of which is incorporated herein by reference in its entirety.

Another aspect of the present invention is directed to transformed host cells having an expression vector comprising any of the nucleic acid molecules described above. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces,* and *Staphylococcus.*

If an eukaryotic expression vector is employed, then the appropriate host cell would be any eukaryotic cell capable of expressing the cloned sequence. Preferably, eukaryotic cells are cells of higher eukaroytes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera *Saccharomyces, Pichia,* and *Kluveromyces.* Preferred yeast hosts are *S. cerevisiae* and *P. pastoris.* Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 1988, 6, 47, Baculovirus Expression Vectors: A Laboratory Manual, O'Reilly et al. (Eds.), W. H. Freeman and Company, New York, 1992, and U.S. Pat. No. 4,879,236, each of which is incorporated herein by reference in its entirety). In addition, the MAX-BAC™ complete baculovirus expression system (Invitrogen) can, for example, be used for production in insect cells.

Another aspect of the present invention is directed to compositions, including pharmaceutical compositions, comprising any of the nucleic acid molecules or recombinant expression vectors described above and an acceptable carrier or diluent. Preferably, the carrier or diluent is pharmaceutically acceptable. Suitable carriers are described in the most recent edition of *Remingtion's Pharmaceutical Sciences*, A. Osol, a standard reference text in this field, which is incorporated herein by reference in its entirety. Preferred examples of such carriers or diluents include, but are not limited to, water, saline, Ringer's solution, dextrose solution, and 5% human serum albumin. Liposomes and non-aqueous vehicles such as fixed oils may also be used. The formulations are sterilized by commonly used techniques.

Another aspect of the present invention is directed to an isolated polypeptide encoded by a nucleic acid molecule described above. In preferred embodiments of the invention, the isolated polypeptide comprises the amino acid sequences set forth in SEQ ID NO:3. Alternatively, the polypeptide is a fragment of the polypeptide encoding SEQ ID NO:3. Preferably, the fragment comprises from about 5 to 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 620 amino acids, from about 621 to about 640 amino acids, from about 641 to about 660 amino acids, from about 661 to about 680 amino acids, from about 681 to about 700 amino acids, from about 701 to about 719 amino acids, and any combinations thereof. The fragment can be located within any portion of SEQ ID NO:3.

In another preferred embodiment of the invention, the polypeptide comprises an amino acid sequence homologous to SEQ ID NO:3 or a fragment thereof as described above. It is to be understood that the present invention included proteins homologous to, and having essentially the same biological properties as, the polypeptides encoded by the nucleotide sequences described herein, i.e., a variant. This definition is intended to encompass isoforms and natural allelic variants of the pak5 genes described herein. These variant forms may result from, for example, alternative splicing or differential expression in different tissue of the same source organism. The variant forms may be characterized by, for example, amino acid insertion(s), deletion(s) or substitution(s). In this connection, a variant form having an amino acid sequence which has at least about 70% sequence homology, at least about 80% sequence homology, preferably about 90% sequence homology, more preferably about 95% sequence homology and most preferably about 98% sequence homology of SEQ ID NO:3 is contemplated as being included in the present invention. A preferred homologous polypeptide comprises at least one conservative amino acid substitution compared to SEQ ID NO:3. Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the pak5 sequence using recombinant DNA techniques.

Alternations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis, which is described by Walder et al., *Gene*, 1986, 42, 133, Bauer et al., *Gene*, 1985, 37, 73, Craik, BioTechniques, January 1985, pp.12–19, Smith et al., Genetic Engineering: Principles and Methods, Plenum Press (1981), and U.S. Pat. Nos. 4,518,584 and 4,737,462, each of which is incorporated herein by reference in its entirety.

Preferably, a PAK5 variant of the present invention will exhibit substantially the biological activity of a naturally occurring PAK5 polypeptide. By "exhibit substantially the biological activity of a naturally occurring PAK5 polypeptide" is meant that PAK5 variants within the scope of the invention can comprise conservatively substituted sequences, meaning that one or more amino acid residues of a PAK5 polypeptide are replaced by different residues that do not alter the secondary and/or tertiary structure of the PAK5 polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges can be found in Bowie et al., *Science*, 1990, 247, 1306–1310, which is incorporated herein by reference in its entirety. Other PAK5 variants which might retain substantially the biological activities of PAK5 are those where amino acid substitutions have been made in areas outside functional regions of the protein.

The polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the polynucleotide sequence so that the polypeptide is translated as a fusion protein comprising the signal peptide. A signal peptide that is functional in the intended host cell promotes extracellular secretion of the polypeptide. Preferably, the signal sequence will be cleaved from the polypeptide upon secretion of the polypeptide from the cell. Thus, preferred fusion proteins can be produced in which the N-terminus of PAK5 is fused to a carrier peptide.

In one embodiment, the polypeptide comprises a fusion protein which includes a heterologous region used to facilitate purification of the polypeptide. Many of the available peptides used for such a function allow selective binding of the fusion protein to a binding partner. A preferred binding partner includes one or more of the IgG binding domains of protein A are easily purified to homogeneity by affinity chromatography on, for example, IgG-coupled Sepharose. Alternatively, many vectors have the advantage of carrying a stretch of histidine residues that can be expressed at the N-terminal or C-terminal end of the target protein. Thus the protein of interest can be recovered by metal chelation chromatography. A nucleotide sequence encoding a recognition site for a proteolytic enzyme such as enterokinase, factor X or, procollagenase or thrombin may immediately precede the sequence for PAK5 to permit cleavage of the fusion protein to obtain the mature PAK5 protein. Additional examples of fusion partners include, but are not limited to, the yeast I-factor, the honeybee melatin leader in sf9 insect cells, 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

The polypeptides of the invention can be used as antigens for raising antibodies against the same and used to screen for compounds that modulate the activity of PAK5. PAK5 can also be used in compositions. Accordingly, the invention relates to PAK5 or an antibody according to the invention for use as a medicament as well as to the use of the molecules in the manufacture of a medicament directed towards conditions wherein PAK5 activity is defective or unregulated: these are expected to include, but are not limited to, cancer, angiogenesis-related diseases, diseases of the central nervous system, diseases due to inappropriate activation of immune responses. The molecules used as medicaments according to the invention may be the polypeptides or antibodies described herein as well as any novel substance identified in a screening method described herein.

In another aspect, the invention provides PAK5 polypeptides with or without associated native pattern glycosylation, acylation, sialylation, or other post-translational modifications. PAK5 expressed in yeast or mammalian expression systems (discussed below) may be similar to or significantly different from a native PAK5 polypeptide in molecular weight and glycosylation pattern. Of course, expression of PAK5 in bacterial expression systems will provide non-glycosylated PAK5.

Another aspect of the present invention is directed to compositions, including pharmaceutical compositions, comprising any of the polypeptides described above and an acceptable carrier or diluent. Preferably, the carrier or diluent is pharmaceutically acceptable. Compositions comprising a polypeptide, as described above, can be used to, for example, induce antibody formation and to induce an immune response for use in, for example, vaccine preparations.

Another aspect of the present invention is directed to methods of producing a polypeptide comprising SEQ ID NO:3, or a homolog or fragment thereof, comprising introducing any of the recombinant expression vectors described above into compatible host cells, growing the host cells under conditions for expression of the polypeptide, and recovering the polypeptide from the host cells. Eukaryotic systems are preferred since they provide a variety of processing mechanisms which result in, for example, glycosylation, carboxy-terminal amidation, oxidation or derivatization of certain amino acid residues, conformational control, and so forth.

The polypeptides of the present invention are preferably provided in an isolated form, are preferably substantially purified, and most preferably are purified to homogeneity. Host cells are preferably lysed and the polypeptide is recovered from the lysate of the host cells. Alternatively, the polypeptide is recovered by purifying the cell culture medium from the host cells, preferably without lysing the host cell. The polypeptides can be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography.

In addition to producing these proteins by recombinant techniques, automated amino acid synthesizers may also be employed to produce PAK5 polypeptides, or fragments a homologous protein thereof.

Another aspect of the present invention is directed to an antibody or antibodies which bind to an epitope on any of the polypeptides described herein. Preferably, the antibody binds to an epitope within SEQ ID NO:3. The antibodies according to the invention can be monoclonal or polyclonal and include individual, allelic, strain or species variants, or fragments thereof, both in their naturally occurring (full-length) forms and recombinants forms. Additionally, the antibodies are raised to the present proteins in either their native configuration or in non-native configurations. Anti-idiotypic antibodies can also be generated.

Hybridomas which produce antibodies that bind to the polypeptides of the invention, and the antibodies themselves, are useful in the isolation and purification of the polypeptides. In addition, antibodies may be specific inhibitors of PAK5 activity. Antibodies which specifically bind to the polypeptides of the invention can be used to purify the protein from natural sources using well known techniques and readily available starting materials. Such antibodies can also be used to purify the protein from material present when producing the protein by recombinant DNA methodology.

Many methods of making antibodies are known to persons skilled in the art. For techniques for preparing monoclonal antibodies, see e.g. Stiites et al (eds.), *Basic and Clinical Immunology* (4$^{th}$ ed.), Lange Medical Publications, Los Altos, Calif., which is incorporated herein by reference in its entirety, and references cited therein. Techniques that involve selection of libraries of recombinant antibodies in phage or similar vectors are described in Huse et al., *Science*, 1989, 246, 1275–1281, which is incorporated herein by reference in its entirety. The production of antibodies and the protein structures of complete, intact antibodies, Fab fragments and F(ab)$_2$ fragments and the organization of the genetic sequences that encode such molecules are well known and are also described, for example, in Harlow, E. and D. Lane (1988) ANTIBODIES: A Laboratory Manual, Cold Spring Harbor Laboratory, Cold Spring Harbor, N.Y., which is incorporated herein by reference. Briefly, for example, a polypeptide of the invention is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the polypeptide, the hybridoma which produces them is cultured to produce a continuous supply of antibodies.

The present invention is also directed to kits, including pharmaceutical kits. The kits can comprise any of the nucleic acid molecules described above, any of the polypeptides described above, or any antibody which binds to a polypeptide of the invention as described above, as well as a negative control. The kit preferably comprises additional components, such as, for example, instructions, solid supports, reagents helpful for quantification, and the like.

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Another aspect of the present invention is directed to methods of identifying compounds which bind to either PAK5 or nucleic acid molecules encoding PAK5, comprising contacting PAK5, or a nucleic acid molecule encoding the same, with a compound, and determining whether the compound binds PAK5, or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology*, 1999, John Wiley & Sons, NY, which is incorporated herein by reference in its entirety. The compounds to be screened include (which may include compounds which are suspected to bind PAK5, or a nucleic acid molecule encoding the same), but are not limited to, extracellular, intracellular, biologic or chemical origin. The PAK5 polypeptide or polynucleotide employed in such a test may either be free in solution, attached to a solid support, borne on a cell surface or located intracellularly. One skilled in the art can, for example, measure the formation of complexes between PAK5 and the compound being tested. Alternatively, one skilled in the art can examine the diminution in complex formation between PAK5 and its substrate caused by the compound being tested.

Another aspect of the present invention is directed to methods of identifying compounds which modulate (i.e., increase or decrease) an activity of PAK5 comprising contacting PAK5 with a compound, and determining whether the compound modifies activity of PAK5. The activity in the presence of the test compared is measured to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using PAK5 in any of a variety of drug screening techniques. The compounds to be screened include (which may include compounds which are suspected to modulate PAK5 activity), but are not limited to, extracellular, intracellular, biologic or chemical origin. The PAK5 polypeptide employed in such a test may be in any form, preferably, free in solution, attached to a solid support, borne on a cell surface, or located intracellularly. One skilled in the art can, for example, measure the formation of complexes between PAK5 and the compound being tested. Alternatively, one skilled in the art can examine the diminution in complex formation between PAK5 and its substrate caused by the compound being tested.

PAK5 is herein predicted to be a serine/threonine protein kinase which, amongst the kinase families known to date, has the highest degree of functional and structural homology to the previously described STE20-like PAK kinases. Compelling evidence for this is present in the primary structure of PAK5 protein (SEQ ID NO:3). For example, SEQ ID NO:3 was used to search the GenBank sequence database using the TBLASTN algorithm within the BLAST series of databases search program. GenBank is the National Institutes of Health (NIH) genetic sequence database, an annotated collection of all publicity available DNA sequences (Benson, D. A. et al., Nucleic Acids Research, vol. 27, 12-7, 1999). There are approximately 3,841,000,000 bases in 4,865,000 sequence records as of October 1999. GenBank is available for searching via several methods, and may be accessed through the internet GenBank website that is maintained by the National Center for Biotechnology Information of the National Library of Medicine of the National Institutes of Health (the website having the URL address: www host server.ncbi.nlm.nih.gov domain name, GenBank directory, GenBankSearch subdirectory). GenBank is part of the International Nucleotide Sequence Database Collaboration, which is comprised of the DNA DataBank of Japan (DDBJ), the European Molecule Biology Laboratory (EMBL), and GenBank at NCBI. These three organizations exchange data on a daily basis. The BLAST algorithm, which stands for Basic Local Alignment Search Tool is suitable for determining sequence similarity (Altschul et al., J. Mol. Biol., 1990, 215, 403–410, which is incorporated herein by reference in its entirety). Software for performing BLAST analyses is publicly available through the National Center for Biotechnology Information (the website having the URL address: www host server, ncbi.nlm.nih.gov domain name). The BLAST algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the work hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T and X determine the sensitivity and speed of the alignment. The BLAST program uses as defaults a word length (W) of 11, the BLOSUM62 scoring matrix (see Henikoff et al., Proc. Natl. Acad. Sci. USA, 1992, 89, 10915–10919, which is incorporated herein by reference in its entirety) alignments (B) of 50, expectation (E) of 10, M=5, N=4, and a comparison of both strands.

The BLAST algorithm (Karlin et al., Proc. Natl. Acad. Sci. USA, 1993, 90, 5873–5787, which is incorporated herein by reference in its entirety) and Gapped BLAST (Altschul et al., *Nuc. Acids Res.*, 1997, 25, 3389, which is incorporated herein by reference in its entirety) perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a pak5 gene or cDNA if the smallest sum probability in comparison of the test nucleic acid to a PAK5 nucleic acid is less than about 1, preferably less than about 0.1., more preferably less than about 0.01, and most preferably less than about 0.001. TBLASTN is a variant of BLAST provided by the NCBI at the GenBank internet site (vide supra) which may be used for comparing amino acid sequences to nucleotide sequences, and which in this case compares the protein query sequence against GenBank nucleotide database dynamically translated in all reading frames.

Searching GenBank using TBLASTN with amino acid sequences reported in SEQ ID NO:3 as query sequence revealed that the first 110 amino acids of PAK5 polypeptide (SEQ IDNO:3) share approximately 66% identity and 83% similarity with the corresponding region of human PAK4: this stretch of sequence includes the presence of a GBD/CRIB domain motif, which in PAK5 corresponds to the residues approximately 11–53 of SEQ ID NO:3. The GBN/CRIB motif is found in all PAKs, as well as in many other proteins that bind RAC and Cdc42, and has been shown to be essential for interaction of proteins with the GTPases (Burbelo et al., J. Biol. Chem., vol 270, 29071–29074, 1995). Aside from this region of homology with PAK4, the remaining N-terminal region of PAK5 (ca. residues 110 to 449 of SEQ ID NO:3), shares no significant homology with any other known protein. The predicted kinase catalytic domain of the novel PAK5 (SEQ ID NO:3 residues approximately 449 to 700) is however highly similar to the kinase domains of the PAK family, and for example has approximately 85% identity and 92% similarity with the kinase domain of human PAK4, approximately 54% identity and 76% similarity with the kinase domain of human PAK3, approximately 54% identity and 75% similarity with the kinase domain of human PAK1, and approximately 53% identity and 73% similarity with the kinase domain of human PAK2. Like all PAK family members, the kinase domain of PAK5 contains the 11 subdomains that are characteristic of serine/threonine protein kinases (for an analysis of kinase subdomain sequences see, e.g. Hanks, S. K. and Quinn, A. M., Methods Enzymol. Vol 200, pp. 38–62; Hardie, G., Hanks, S. et al. The Protein Kinase Factsbook, Academic Press Inc; ISBN: 0123247195). Residue positions 456–463 (GEGSTGIV) (SEQ ID NO:15) of PAK5 for instance, correspond to the consensus kinase subdomain I GxGxxGxV (SEQ ID NO:16). Subdomain II is involved in the phosphotransfer reaction and is identified by an invariant lysine in the tripeptide sequence AxK. With regard to the novel kinase SEQ ID NO:3, subdomain II is found in residues 476–478 (AVK). Subdomains VI through IX, characterized by a large number of highly conserved residues, form the central core of catalytic activity. SEQ ID NO:3 comprises Region VIB contains the consensus sequence HRDLxxxN (SEQ ID NO:17); SEQ ID NO:3 in this region is HRDIKSIS (SEQ ID NO:18) (wherein the substitutions of Ile for Lue and of Ser for Asn are conservative) as well as the invariant or nearly invariant residues $Asp_{586}$, $Phe_{587}$ and $Gly_{588}$ in subdomain VII; all of which have been implicated in ATP binding. The conserved D in subdomain VII ($Asp_{586}$) functions to orient the γ-phosphate of the ATP for transfer. Subdomain VII of SEQ ID NO:3 contains the highly conserved APE sequence (residues 610–613), with Glu corresponding to the invariant $Glu_{613}$. The sequence DxWS/AxG (SEQ ID NO:19) of subdomain IX is represented by amino acid positions 625–630 of SEQ ID NO:3 (DIWSLG) (SEQ ID NO:20). This region forms a large α-helix and the initial Asp of the consensus sequence serves to stabilize the catalytic loop by hydrogen bonding.

The activity of PAK5 polypeptide of the invention can therefore be determined by, for example, assaying for kinase activity of PAK5. In such assays PAK5 polypeptide or a fragment thereof produced by recombinant means as described above is contacted with a substrate in the presence of a suitable phosphate donor, preferably ATP, containing radiolabeled phosphate, and PAK5-dependent incorporation of radiolabel into the substrate is measured. By 'substrate', one means any substance containing a suitable hydroxyl moiety that acts as an acceptor for the γ-phosphate group transferred from a donor molecule such as ATP in a reaction catalyzed by PAK5. The substrate may be an endogenous substrate of PAK5, i.e. a naturally-occurring substance that is phosphorylated in unmodified cells by naturally-occurring PAK5, or any other substance that is not normally phosphorylated by PAK5 in a physiological situation, by that may be phosphorylated by PAK5 in the reaction conditions employed. Preferably, the substrate is a protein or peptide, and preferably, the phosphorylation reaction occurs on a substrate serine or threonine residue. It is well-known to those skilled in the art that non-natural substrates can act as suitable substrates in kinase assays such as that described above, and examples of specific substrates which are commonly employed in such assays include, but are not limited to, histone proteins any mylein basic protein. It is also well known to those skilled in the art that detection of kinase-dependent substrate phosphorylation can be effected by a number of means other than measurement of radiolabeled phosphate incorporation into the substrate. For example, incorporation of phosphate groups can affect physicochemical properties of the substrate, such as electrophoretic mobility, light absorbance, fluorescence and/or phosphorescence, chromatographic properties, and so on. Such alterations of substrate physicochemical properties can be readily measured by one skilled in the art, and used as an indicator of kinase activity. Alternatively, it is also well known that monoclonal or polyclonal antibodies can be generated which selectively recognize phosphorylated forms of the substrate, and thus the degree of binding of such antibodies to substrate subsequent to the kinase reaction can be used as an indirect method of determining kinase activity. Furthermore, it is known that many kinases, including PAK kinases, possess the capacity to phosphorylated residues on the same kinase molecule. Such phosphorylation reactions are termed autophosphorylation, and therefore measurement of incorporation of phosphate into PAK5 itself catalyzed by the same may also be used to monitor PAK5 activity. Kinase assays such as those described above can be performed not only using purified, or partially recombinant PAK5, but also PAK5 which is purified from cells which naturally express the protein using purification procedures such as those described above.

In addition, PAK5 activity may not be measured solely by assaying the kinase activity, but also by the detection of events that lead to, or are consequent of PAK5 activity in intact cells, or cell lysates, or in systems in which signaling events are reconstituted in vitro. For example, it is known that PAK proteins bind to, and are activated by GTP-binding proteins such as Rac and Cdc42. Thus detection of interaction of PAK5 with naturally occurring activators such as Rac/Cdc42, and/or substrates may also be used as an indicator of PAK5 activity.

In order to identify compounds capable of modulating PAK5 activity, assays such as, but not limited to, those described above can be performed in the presence and absence of test compounds.

Other assays can be used to examine enzymatic activity including, but not limited to, photometric, radiometric, HPLC, electrochemical, and the like, which are described in, for example, *Enzyme Assays: A Practical Approach*, eds. R. Eisenthal and M. J. Danson, 1992, Oxford University Press, which is incorporated herein by reference in its entirety.

In preferred embodiments of the invention, methods of screening for compounds which modulate PAK5 activity comprise contacting the compound with PAK5 and assaying for the presence of a complex between the compound and PAK5. In such assays, PAK5 is typically labeled. After suitable incubation, free PAK5 is separated from that present in bound form, and the amount of free or uncomplexed label is a measure of the ability of the particular compound to bind to PAK5.

In another embodiment of the invention, high throughput screening for compounds having suitable binding affinity to PAK5 is employed. Briefly, large numbers of different small peptide test compounds are synthesized on a solid substrate. The peptide test compounds are contacted with PAK5 and washed. Bound PAK5 is then detected by methods well known in the art.

Purified polypeptides of the invention can also be coated directly onto plates for use in the aforementioned drug screening techniques. In addition, non-neutralizing antibodies can be used to capture the protein and immobilize it on the solid support.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide which shares one or more antigenic determinants with PAK5. Radiolabeled competitive binding studies are described in A. H. Lin et al. *Antimicrobial Agents and Chemotherapy*, 1997, vol. 41, no. 10. pp. 2127–2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to PAK5 of the invention, but which are smaller and exhibit a longer half-life than PAK5 in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

As discussed above, comparison of the protein sequence of the present invention with the sequences present in all the available databases showed a significant homology with the GBD/CRIB domain and serine/threonine protein kinase domains. Accordingly, computer modeling can be used to develop a putative tertiary structure of the proteins of the invention based on the available information of other GBD/CRIB or Kinase domain proteins. Thus, novel enzyme inhibitors based on the predicted structure of PAK5 can be designed.

In a particular embodiment, the novel molecules identified by the screening methods according to the invention are low molecular weight organic molecules, in which case a composition or pharmaceutical composition can be prepared thereof for oral intake, such as in tablets. The composition, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in Remington's Pharmaceutical Sciences, $16^{th}$ edition, Osol, A (ed), 1980, which is incorporated herein by reference in its entirety.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

The present compounds and methods, including nucleic acid molecules, polypeptides, antibodies, compounds identified by the screening methods described herein, have a variety of pharmaceutical applications and my be used, for example, to treat or prevent unregulated cellular growth, such as cancer cell and tumor growth. In a particular embodiment, the present molecules are used in gene therapy. For a review of gene therapy procedures, see e.g. Anderson, *Science*, 1992, 256, 808–813, which is incorporated herein by reference in its entirety.

TABLE 2

Sequence ID NO: 1    pak5

```
   1 gagaccggga acatggcgct gggagcnctg tagcagctga aaggggctg aggcaccgcc
  61 gcttcgctga cagccggcca ccagatgttc atgcattcta gagaaagtgg aaaacttaga
 121 agcctaatta atgactgtct tctggacctc tgagaccatg tttctagtgt tttccgtgga
 181 atattatcag aaatacactg tggtgaaatg cttccacctc ttgctaaaat gaacactgag
 241 gaaaaatgaa gaagactgac aagcaccagc gaaaagttgc agaatagaaa tagccacact
 301 cctctggagt cttaattca tccacagcca tcatataaag gttttggcat catgtttggg
 361 aagaaaaaga aaagattga aatatctggc ccgtccaact ttgaacacag ggttcatact
 421 gggtttgatc cacaagagca gaagtttacc ggccttcccc agcagtggca cagcctgtta
 481 gcagatacgg ccaacaggcc aaagcctatg gtggacccctt catgcatcac acccatccag
 541 ctggctccta tgaagacaat cgttagagga acaaaccct gcaaggaaac ctccatcaac
 601 ggcctgctag aggattttga acatctcg gtgactcgct ccaactccct aaggaaagaa
 661 agcccaccca ccccagatca gggagcctcc agccacggtc caggccacgc ggaagaaaat
 721 ggcttcatca ccttctccca gtattccagc gaatccgata ctactgctga ctacacgacc
 781 gaaaagtaca gggagaagag tctctatgga gatgatctgg atccgtatta tagaggcagc
 841 cacgcagcca agcaaaatgg gcacgtaatg aaaatgaagc acggggaggc ctactattct
 901 gaggtgaagc ctttgaaatc cgattttgcc agattttctg ccgattatca ctcacatttg
 961 gactcactga gcaaaccaag tgaatacagt gacctcaagt gggagtatca gagagcctcg
1021 agtagctccc ctctggatta ttcattccaa ttcacacctt ctagaactgc agggaccagc
1081 gggtgctcca aggagagcct ggcgtacagt gaaagtgaat ggggacccag cctggatgac
1141 tatgacagga ggccaaagtc ttcgtacctg aatcagacaa gccctcagcc caccatgcgg
1201 cagaggtcca ggtcaggctc gggactccag gaaccgatga tgccatttgg agcaagtgca
1261 tttaaaaccc atccccaagg acactcctac aactcctaca cctaccctcg cttgtccgag
1321 cccacaatgt gcattccaaa ggtggattac gatcgagcac agatggtcct cagccctcca
1381 ctgtcagggt ctgacaccta ccccagggc cctgccaaac tacctcaaag tcaaagcaaa
1441 tcgggctatt cctcaagcag tcaccagtac ccgtctgggt accacaaagc caccttgtac
1501 catcaccct ccctgcagag cagttcgcag tacatctcca cggcttccta cctgagctcc
1561 ctcagcctct catccagcac ctaccccgcg cccagctggg gctcctcctc cgaccagcag
1621 ccctccaggg tgtcccatga acagtttcgg gcggccctgc agctggtggt cagcccagga
1681 gaccccaggg aatacttggc caactttatc aaaatcgggg aaggctcaac cggcatcgta
1741 tgcatcggca ccgagaaaca cacagggaaa caagttgcag tgaagaaaat ggacctccgg
1801 aagcaacaga gacgagaact gcttttcaat gaggtcgtga tcatgcggga ttaccaccat
1861 gacaatgtgg ttgacatgta cagcagctac cttgtcggcg atgagctctg ggtggtcatg
1921 gagtttctag aaggtggtgc cttgacagac attgtgactc acaccagaat gaatgaagaa
1981 cagatagcta ctgtctgcct gtcagttctg agagctctct cctaccttca taaccaagga
2041 gtgattcaca gggacataaa aagtgactcc atcctcctga caagcgatgg ccggataaag
2101 ttgtctgatt ttggtttctg tgctcaagtt tccaaagagg tgccgaagag gaaatcattg
2161 gttggcactc cctactggat ggcccctgag ctgattccta ggctacctta tgggacagag
2221 gtggacatct ggtccctcgg gatcatggtg atagaaatga ttgatggcga gccccctac
```

TABLE 2-continued

```
2281 ttcaatgagc ctcccctcca ggcgatgcgg aggatccggg acagtttacc tccaagagtg
2341 aaggacctac acaaggtttc ttcagtgctc cggggattcc tagacttgat gttggtgagg
2401 gagccctctc agagagcaac agcccaggaa ctcctcggac atccattctt aaaactagca
2461 ggtccaccgt cttgcatcgt cccctcatg agacaataca ggcatcactg a
```

Sequence ID NO: 2 pak5 ORF

```
   1 atgtttggga agaaaaagaa aaagattgaa atatctggcc cgtccaactt tgaacacagg
  61 gttcatactg ggtttgatcc acaagagcag aagtttaccg gccttcccca gcagtggcac
 121 agcctgttag cagatacggc caacaggcca agcctatgg tggacccttc atgcatcaca
 181 cccatccagc tggctcctat gaagacaatc gttagaggaa acaaaccctg caaggaaacc
 241 tccatcaacg gcctgctaga ggattttgac aacatctcgg tgactcgctc caactcccta
 301 aggaaagaaa gcccacccac cccagatcag ggagcctcca gccacggtcc aggccacgcg
 361 gaagaaaatg gcttcatcac cttctcccag tattccagcg aatccgatac tactgctgac
 421 tacacgaccg aaaagtacag ggagaagagt ctctatggag atgatctgga tccgtattat
 481 agaggcagcc acgcagccaa gcaaaatggg cacgtaatga aaatgaagca cggggaggcc
 541 tactattctg aggtgaagcc tttgaaatcc gattttgcca gattttctgc cgattatcac
 601 tcacatttgg actcactgag caaaccaagt gaatacagtg acctcaagtg ggagtatcag
 661 agagcctcga gtagctcccc tctggattat tcattccaat tcacaccttc tagaactgca
 721 gggaccagcg ggtgctccaa ggagagcctg gcgtacagtg aaagtgaatg gggacccagc
 781 ctggatgact atgacaggag gccaaagtct tcgtacctga atcagacaag ccctcagccc
 841 accatgcggc agaggtccag gtcaggctcg ggactccagg aaccgatgat gccatttgga
 901 gcaagtgcat taaaaccca tccccaagga cactcctaca actcctacac ctaccctcgc
 961 ttgtccgagc ccacaatgtg cattccaaag gtggattacg atcgagcaca gatggtcctc
1021 agccctccac tgtcagggtc tgacacctac ccagggggcc ctgccaaact acctcaaagt
1081 caaagcaaat cgggctattc ctcaagcagt caccagtacc cgtctgggta ccacaaagcc
1141 accttgtacc atcacccctc cctgcagagc agttcgcagt acatctccac ggcttcctac
1201 ctgagctccc tcagcctctc atccagcacc tacccgccgc cagctggggg ctcctcctcc
1261 gaccagcagc cctccagggt gtcccatgaa cagtttcggg cggccctgca gctggtggtc
1321 agcccaggag accccaggga atacttggcc aactttatca aaatcgggga aggctcaacc
1381 ggcatcgtat gcatcggcac cgagaaacac acagggaaac aagttgcagt gaagaaaatg
1441 gacctccgga gcaacagag cgagaactg cttttcaatg aggtcgtgat catgcgggat
1501 taccaccatg acaatgtggt tgacatgtac agcagctacc ttgtcggcga tgagctctgg
1561 gtggtcatgg agtttctaga aggtggtgcc ttgacagaca ttgtgactca caccagaatg
1621 aatgaagaac agatagctac tgtctgcctg tcagttctga gagctctctc ctaccttcat
1681 aaccaaggag tgattcacag ggacataaaa agtgactcca tcctcctgac aagcgatggc
1741 cggataaagt tgtctgattt tggtttctgt gctcaagttt ccaagagggt gccgaagagg
1801 aaatcattgg ttggcactcc ctactggatg cccctgagc tgattctag ctaccttat
1861 gggacagagg tggacatctg gtccctcggg atcatggtga tagaaatgat tgatggcgag
1921 ccccctact tcaatgagcc tcccctccag gcgatgcgga ggatccggga cagtttacct
1981 ccaagagtga aggacctaca caaggttcct tcagtgctcc ggggattcct agacttgatg
```

TABLE 2-continued

```
2041 ttggtgaggg agccctctca gagagcaaca gcccaggaac tcctcggaca tccattctta
2101 aaactagcag gtccaccgtc ttgcatcgtc ccctcatga gacaatacag gcatcac
```

Sequence ID NO: 3 PAK5 amino acid sequence

```
  1 MFGKKKKKIE ISGPSNFEHR VHTGFDPQEQ KFTGLPQQWH SLLADTANRP KPMVDPSCIT
 61 PIQLAPMKTI VRGNKPCKET SINGLLEDFD NISVTRSNSL RKESPPTPDQ GASSHGPGHA
121 EENGFITFSQ YSSESDTTAD YTTEKYREKS LYGDDLDPYY RGSHAAKQNG HVMKMKHGEA
181 YYSEVKPLKS DFARFSADYH SHLDSLSKPS EYSDLKWEYQ RASSSSPLDY SFQFTPSRTA
241 GTSGCSKESL AYSESEWGPS LDDYDRRPKS SYLNQTSPQP TMRQRSRSGS GLQEPMMPFG
301 ASAFKTHPQG HSYNSYTYPR LSEPTMCIPK VDYDRAQMVL SPPLSGSDTY PRGPAKLPQS
361 QSKSGYSSSS HQYPSGYHKA TLYHHPSLQS SSQYISTASY LSSLSLSSST YPPPSWGSSS
421 DQQPSRVSHE QFRAALQLVV SPGDPREYLA NFIKIGEGST GIVCIGTEKH TGKQVAVKKM
481 DLRKQQRREL LFNEVVIMRD YHHDNVVDMY SSYLVGDELW VVMEFLEGGA LTDIVTHTRM
541 NEEQIATVCL SVLRALSYLH NQGVIHRDIK SDSILLTSDG RIKLSDFGFC AQVSKEVPKR
601 KSLVGTPYWM APELISRLPY GTEVDIWSLG IMVIEMIDGE PPYFNEPPLQ AMRRIRDSLP
661 PRVKDLHKVS SVLRGFLDLM LVREPSQRAT AQELLGHPFL KLAGPPSCIV PLMRQYRHH
```

SEQ ID NO: 4 Human PAK1 CDS from GenBank

```
   1 atgtcaaata acggcctaga cattcaagac aaaccccag ccctccgat gagaaatacc
  61 agcactatga ttggagccgg cagcaaagat gctggaaccc taaaccatgg ttctaaacct
 121 ctgcctccaa acccagagga gaagaaaaag aaggaccgat tttaccgatc cattttacct
 181 ggagataaaa caaataaaaa gaaagagaaa gagcggccag agatttctct cccttcagat
 241 tttgaacaca caattcatgt cggttttgat gctgtcacag gggagtttac cggaatgcca
 301 gagcagtggg cccgcttgct tcagacatca aatatcacta agtcggagca aagaaaaac
 361 ccgcaggctg ttctggatgt gttggagttt tacaactcga gaagacatc caacagccag
 421 aaatacatga gctttacaga taagtcagct gaggattaca attcttctaa tgccttgaat
 481 gtgaaggctg tgtctgagac tcctgcagtg ccaccagttt cagaagatga ggatgatgat
 541 gatgatgatg ctaccccacc accagtgatt gctccacgcc agagcacac aaaatctgta
 601 tacacacggt ctgtgattga accacttcct gtcactccaa ctcgggacgt ggctacatct
 661 cccatttcac ctactgaaaa taacaccact ccaccagatg ctttgaccct taatactgag
 721 aagcagaaga gaagcctaa aatgtctgat gaggagatct tggagaaatt acgaagcata
 781 gtgagtgtgg gcgatcctaa gaagaaatat acacggtttg agaagattgg acaaggtgct
 841 tcaggcaccg tgtacacagc aatggatgtg ccacaggac aggaggtggc cattaagcag
 901 atgaatcttc agcagcagcc caagaaagag ctgattatta tgagatcct ggtcatgagg
 961 gaaaacaaga acccaaacat tgtgaattac ttggacagtt acctcgtggg agatgagctg
1021 tgggttgtta tggaatactt ggctggaggc tccttgacag atgtggtgac agaaacttgc
1081 atggatgaag ccaaattgc agctgtgtgc cgtgagtgtc tgcaggctct ggagtctttg
1141 cattcgaacc aggtcattca cagagacatc aagagtgaca atattctgtt gggaatggat
1201 ggctctgtca agctaactga ctttggattc tgtgcacaga taaccccaga gcagagcaaa
1261 cggagcacca tggtaggaac cccatactgg atggcaccag aggttgtgac acgaaaggcc
1321 tatgggccca aggttgacat ctggtccctg ggcatcatgg ccatcgaaat gattgaaggg
```

TABLE 2-continued

```
1381 gagcctccat acctcaatga aaaccctctg agagccttgt acctcattgc caccaatggg
1441 accccagaac ttcagaaccc agagaagctg tcagctatct tccgggactt tctgaaccgc
1501 tgtctcgaga tggatgtgga agagagaggt tcagctaaag agctgctaca gcatcaattc
1561 ctgaagattg ccaagcccct ctccagcctc actccactga ttgctgcagc taaggaggca
1621 acaaagaaca atcactaa
```

SEQ ID NO: 5 Human PAK2 CDS from GenBank

```
   1 atgtctgata acggagaact ggaagataag cctccagcac ctcctgtgcg aatgagcagc
  61 accatctttta gcactggagg caaagaccct ttgtcagcca atcacagttt gaaacctttg
 121 ccctctgttc cagaagagaa aaagcccagg cataaaatca tctccatatt ctcaggcaca
 181 gagaaaggaa gtaaaagaa agaaaaggaa cggccagaaa tttctcctcc atctgatttt
 241 gagcacacca tccatgttgg ctttgatgct gttactggag aattcactgg catgccagaa
 301 cagtgggctc gattactaca gacctccaat atcaccaaac tagagcaaaa gaagaatcct
 361 caggctgtgc tggatgtcct aaagttctac gactccaaca cagtgaagca gaaatatctg
 421 agctttactc ctcctgagaa agatggcctt ccttctggaa cgccagcact gaatgccaag
 481 ggaacagaag cacccgcagt agtgacagag gaggaggatg atgatgaaga actgctcct
 541 cccgttattg ccccgcgacc ggatcatacg aaatcaattt acacacggtc tgtaattgac
 601 cctgttcctg caccagttgg tgattcacat gttgatggtg ctgccaagtc tttagacaaa
 661 cagaaaaaga agcctaagat gacagatgaa gagattatgg agaaattaag aactatcgtg
 721 agcataggtg accctaagaa aaatataca agatatgaaa aaattggaca agggcttct
 781 ggtacagttt tcactgctac tgacgttgca ctgggacagg aggttgctat caaacaaatt
 841 aatttacaga aacagccaaa gaaggaactg atcattaacg agattctggt gatgaaagaa
 901 ttgaaaaatc ccaacatcgt taactttttg gacagttacc tggtaggaga tgaattgttt
 961 gtggtcatgg aataccttgc tgggggtca ctcactgatg tggtaacaga acagcttgc
1021 atggatgaag cacagattgc tgctgtatgc agagagtgtt tacaggcatt ggagttttta
1081 catgctaatc aagtgatcca cagagacatc aaaagtgaca atgtactttt gggaatggaa
1141 ggatctgtta agctcactga ctttggtttc tgtgcccaga tcaccccga gcagagcaaa
1201 cgcagtacca tggtcggaac gccatactgg atggcaccag aggtggttac acggaaagct
1261 tatggcccta aagtcgacat atggtctctg ggtatcatgg ctattgagat ggtagaagga
1321 gagcctccat acctcaatga aaatcccttg agggccttgt acctaatagc aactaatgga
1381 accccagaac ttcagaatcc agagaaactt tccccaatat ttcgggattt cttaaatcga
1441 tgttttggaaa tggatgtgga aaaagggggt tcagccaaag aattattaca gcatccttc
1501 ctgaaactgg ccaaaccgtt atctagcttg acaccactga tcatggcagc taagaagca
1561 atgaagagta accgttaa
```

SEQ ID NO: 6 Human PAK3 CDS from GenBank

```
   1 atgtctgacg gtctggataa tgaagagaaa ccccggctc ctccactgag gatgaatagt
  61 aacaaccggg attcttcagc actcaaccac agctccaaac cacttcccat ggcccctgaa
 121 gagaagaata aaaagccag gcttcgctct atcttcccag gaggagggga taaaaccaat
 181 aagaagaagg agaaagagcg cccagagatc tctcttcctt cagactttga gcatacgatt
```

TABLE 2-continued

```
 241 catgtggggt tgatgcagt caccggggaa tcactggaa ttccagagca atgggcacga
 301 ttactccaaa cttccaacat aacaaaattg aacagaaga agaacccaca agctgttcta
 361 gatgttctca aattctatga ttccaaagaa acagtcaaca accagaaata catgagcttt
 421 acatcaggag ataaaagtgc acatggatac atagcagccc atccttcgag tacaaaaaca
 481 gcatctgagc ctccattggc ccctcctgtg tctgaagaag aagatgaaga ggaagaagaa
 541 gaagaagatg aaaatgagcc accaccagtt atcgcaccaa gaccagagca tacaaaatca
 601 atctatactc gttctgtggt tgaatccatt gcttcaccag cagtaccaaa taaagaggtc
 661 acaccaccct ctgctgaaaa tgccaattcc agtactttgt acaggaacac agatcggcaa
 721 agaaaaaaat ccaagatgac agatgaggag atcttagaga agctaagaag cattgtgagt
 781 gttgggggacc caaagaaaaa atacacaaga ttttgaaaaa ttggtcaagg ggcatcaggt
 841 actgtttata cagcactaga cattgcaaca ggacaagagg tggccataaa gcagatgaac
 901 cttcaacagc aacccaagaa ggaattaatt attaatgaaa ttctggtcat gagggaaaat
 961 aagaaccta atattgttaa ttatttagat agctacttgg tgggtgatga actatgggta
1021 gtcatggaat acttggctgg tggctctctg actgatgtgg tcacagagac ctgtatggat
1081 gaaggacaga tagcagctgt ctgcagagag tgcctgcaag cttttggattt cctgcactca
1141 aaccaggtga tccatagaga tataaagagt gacaatattc ttctcgggat ggatggctct
1201 gttaaattga ctgactttgg gttctgtgcc cagatcactc ctgagcaaag taaacgaagc
1261 actatggtgg gaaccccata ttggatggca cctgaggtgg tgactcgaaa agcttatggt
1321 ccgaaagttg atatctggtc tcttggaatt atggcaattg aaatggtgga aggtgaaccc
1381 ccttacctta tgaaaaatcc actcaggggca ttgtatctga tagccactaa tggaactcca
1441 gagctccaga atcctgagag actgtcagct gtattccgtg acttttttaaa tcgctgtctt
1501 gagatggatg tggataggcg aggatctgcc aaggagcttt tgcagcatcc attttttaaaa
1561 ttagccaagc ctctctccag cctgactcct ctgattatcg ctgcaaagga agcaattaag
1621 aacagcagcc gctaa
```

SEQ ID NO: 7 Human PAK4 CDS from GenBank

```
   1 atgtttggga agaggaagaa gcgggtggag atctccgcgc cgtccaactt cgagcaccgc
  61 gtgcacacgg gcttcgacca gcacgagcag aagttcacgg ggctgccccg ccagtggcag
 121 agcctgatcg aggagtcggc tcgccggccc aagcccctcg tcgaccccgc ctgcatcacc
 181 tccatccagc ccggggcccc caagaccatc gtgcggggca gcaaaggtgc caaagatggg
 241 gccctcacgc tgctgctgga cgagtttgag aacatgtcgg tgacacgctc caactccctg
 301 cggagagaca gcccgccgcc gcccgcccgt gcccgccagg aaaatgggat gccagaggag
 361 ccggccacca cggccagagg gggcccaggg aaggcaggca gccgaggccg gttcgccggt
 421 cacagcgagg caggtggcgg cagtggtgac aggcgacggg cggggccaga gaagaggccc
 481 aagtcttcca gggagggctc aggggggtccc caggagtcct cccgggacaa cgcccccctc
 541 tccgggcctg atgtcggcac ccccagcct gctggtctgg ccagtggggc gaaactggca
 601 gctggccggc cttaacac ctacccgagg gctgacacgg accacccatc ccggggtgcc
 661 caggggggagc ctcatgacgt ggcccctaac gggccatcag cggggggcct ggccatcccc
 721 cagtcctcct cctcctcctc ccggcctccc acccgagccc gaggtgcccc cagccctgga
 781 gtgctgggac cccacgcctc agagccccag ctggccccctc cagcctgcac cccgccgcc
```

TABLE 2-continued

```
 841 cctgctgttc ctgggccccc tggccccgc tcaccacagc gggagccaca gcgagtatcc
 901 catgagcagt tccgggctgc cctgcagctg gtggtggacc caggcgaccc ccgctcctac
 961 ctggacaact tcatcaagat tggcgagggc tccacgggca tcgtgtgcat cgccaccgtg
1021 cgcagctcgg gcaagctggt ggccgtcaag aagatggacc tgcgcaagca gcagaggcgc
1081 gagctgctct tcaacgaggt ggtaatcatg agggactacc agcacgagaa tgtggtggag
1141 atgtacaaca gctacctggt gggggacgag ctctgggtgg tcatggagtt cctggaagga
1201 ggcgccctca ccgacatcgt cacccacacc aggatgaacg aggagcagat cgcagccgtg
1261 tgccttgcag tgctgcaggc cctgtcggtg ctccacgccc agggcgtcat ccaccgggac
1321 atcaagagcg actcgatcct gctgacccat gatggcaggg tgaagctgtc agactttggg
1381 ttctgcgccc aggtgagcaa ggaagtgccc cgaaggaagt cgctggtcgg cacgccctac
1441 tggatggccc cagagctcat ctcccgcctt ccctacgggc cagaggtaga catctggtcg
1501 ctggggataa tggtgattga gatggtggac ggagagcccc cctacttcaa cgagccaccc
1561 ctcaaagcca tgaagatgat tcgggacaac ctgccacccc gactgaagaa cctgcacaag
1621 gtgtcgccat ccctgaaggg cttcctggac cgcctgctgg tgcgagaccc tgcccagcgg
1681 gccacggcag ccgagctgct gaagcaccca ttcctggcca aggcagggcc gcctgccagc
1741 atcgtgcccc tcatgcgcca gaaccgcacc agatga
```

SEQ ID NO: 8 Incyte template 067594.1

```
  1 gagaccggga acatggcgct gggagcnctg tagcagctga gaagggctg aggcaccgcc
 61 gcttcgctga cagccggcca ccagatgttc atgcattcta gagaaagtgg aaaacttaga
121 agcctaatta atgactgtct tctggacctc tgagaccatg tttctagtgt tttccgtgga
181 atattatcag aaatacactg tggtgaaatg cttccacctc ttgctaaaat gaacactgag
241 gaaaatgaa gaagactgac aagcaccagc gaaaagttgc agaatagaaa tagccacact
301 cctctggagt ctttaattca tccacagcca tcatataaag gttttggcat catgtttggg
361 aagaaaaaga aaagattga aatatctggc ccgtccaact ttgaacacag ggttcatact
421 gggtttgatc cacaagagca gaagtttacc ggccttcccc agcagtggca cagcctgtta
481 gcagatacgg ccaacaggcc aaagcctatg gtggacccct catgcatcac acccatccag
541 ctggctccta tgaagacatc gttagaggaa acaaaccctg c
```

SEQ ID NO: 9 = gcatcatgtt tgggaagaaa—primer sequence
SEQ ID NO: 10 = a(g/c)ctc(a/t)gg(t/g)g ccatcca(g/a)ta—primer sequence
SEQ ID NO: 11 Insert sequence from first PCR

```
  1 gcatcatgtt tgggaagaaa aagaaaaaga ttgaaatatc tggcccgtcc aactttgaac
 61 acagggttca tactgggttt gatccacaag agcagaagtt taccggcctt ccccagcagt
121 ggcacagcct gttagcagat acggccaaca ggccaaagcc tatggtggac ccttcatgca
181 tcacacccat ccagctggct cctatgaaga caatcgttag aggaaacaaa ccctgcaagg
241 aaacctccat caacggcctg ctagaggatt ttgacaacat ctcggtgact cgctccaact
301 cccctaaggaa agaaagccca cccacccag atcaggagc ctccagccac ggtccaggcc
361 acgcggaaga aaatggcttc atcaccttct cccagtattc cagcgaatcc gatactactg
421 ctgactacac gaccgaaaag tacagggaga agagtctcta tggagatgat ctggatccgt
481 attatagagg cagccacgca gccaagcaaa atgggcacgt aatgaaaatg aagcacgggg
```

TABLE 2-continued

```
 541 aggcctacta ttctgaggtg aagcctttga aatccgattt tgccagattt tctgccgatt
 601 atcactcaca tttggactca ctgagcaaac caagtgaata cagtgacctc aagtgggagt
 661 atcagagagc ctcgagtagc tcccctctgg attattcatt ccaattcaca ccttctagaa
 721 ctgcagggac cagcgggtgc tccaaggaga gcctggcgta cagtgaaagt gaatggggac
 781 ccagcctgga tgactatgac aggaggccaa agtcttcgta cctgaatcag acaagccctc
 841 agcccaccat gcggcagagg tccaggtcag gctcgggact ccaggaaccg atgatgccat
 901 ttggagcaag tgcatttaaa acccatcccc aaggacactc ctacaactcc tacacctacc
 961 ctcgcttgtc cgagcccaca atgtgcattc caaaggtgga ttacgatcga gcacagatgg
1021 tcctcagccc tccactgtca gggtctgaca cctaccccag gggccctgcc aaactacctc
1081 aaagtcaaag caaatcgggc tattcctcaa gcagtcacca gtacccgtct gggtaccaca
1141 aagccacctt gtaccatcac ccctccctgc agagcagttc gcagtacatc tccacggctt
1201 cctacctgag ctccctcagc ctctcatcca gcacctaccc gccgcccagc tggggctcct
1261 cctccgacca gcagccctcc agggtgtccc atgaacagtt tcgggcggcc ctgcagctgg
1321 tggtcagccc aggagacccc agggaatact tggccaactt tatcaaaatc ggggaaggct
1381 caaccggcat cgtatgcatc ggcaccgaga aacacacagg gaaacaagtt gcagtgaaga
1441 aaatggacct ccggaagcaa cagagacgag aactgctttt caatgaggtc gtgatcatgc
1501 gggattacca ccatgacaat gtggttgaca tgtacagcag ctaccttgtc ggcgatgagc
1561 tctgggtggt catggagttt ctagaaggtg gtgccttgac agacattgtg actcacacca
1621 gaatgaatga agaacagata gctactgtct gcctgtcagt tctgagagct ctctcctacc
1681 ttcataacca aggagtgatt cacagggaca taaaaagtga ctccatcctc ctgacaagcg
1741 atggccggat aaagttgtct gattttggtt tctgtgctca agtttccaaa gaggtgccga
1801 agaggaaatc attggttggc actccctact ggatggcccc tgagct
```

SEQ ID NO: 12 Deduced from sequences within GenBank ACCESSION AL031652

```
  1 ataaagttgt ctgattttgg tttctgtgct caagtttcca aagaggtgcc gaagaggaaa
 61 tcattggttg gcactcccta ctggatggcc cctgaggtga tttctaggct accttatggg
121 acagaggtgg acatctggtc cctcgggatc atggtgatag aaatgattga tggcgagccc
181 ccctacttca atgagcctcc cctccaggcg atgcggagga tccgggacag tttacctcca
241 agagtgaagg acctacacaa ggtttcttca gtgctccggg gattcctaga cttgatgttg
301 gtgagggagc cctctcagag agcaacagcc caggaactcc tcggacatcc attcttaaaa
361 ctagcaggtc caccgtcttg catcgtcccc ctcatgagac aatacaggca tcactga
```

SEQ ID NO: 13 = gagaccggga acatggcgct—primer sequence (sense)

SEQ ID NO: 14 = tcagtgatgc ctgtattgtc tc—primer sequence (antisense)

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Examples 1–3 and 6–7 presented below are actual examples, while examples 4, 5 and 8–10 are prophetic.

FIB. 1A. Kinase assay performed with histone myelin basic protein (MBP) as substrate. Methodology was as described in Example 3. Lanes 1 and 2 correspond to immunoprecipitates from cells transfected with vector encoding PAK5. Lane 3 and 4 correspond to immunoprecipitates from cells transfected with empty control vector, In lanes 1 and 3, MBP was present in the kinase reaction, while in lanes 2 and 4, MBP was absent. Bars on the left hand side of the figure indicate the approximate positions of molecular weight markers, the sizes of which, from top to bottom were 100, 80, 50, 35, and 28 kDa. Note that in the presence of MBP, PAK5 shows strong autophosphorylation.

Figure 1A:
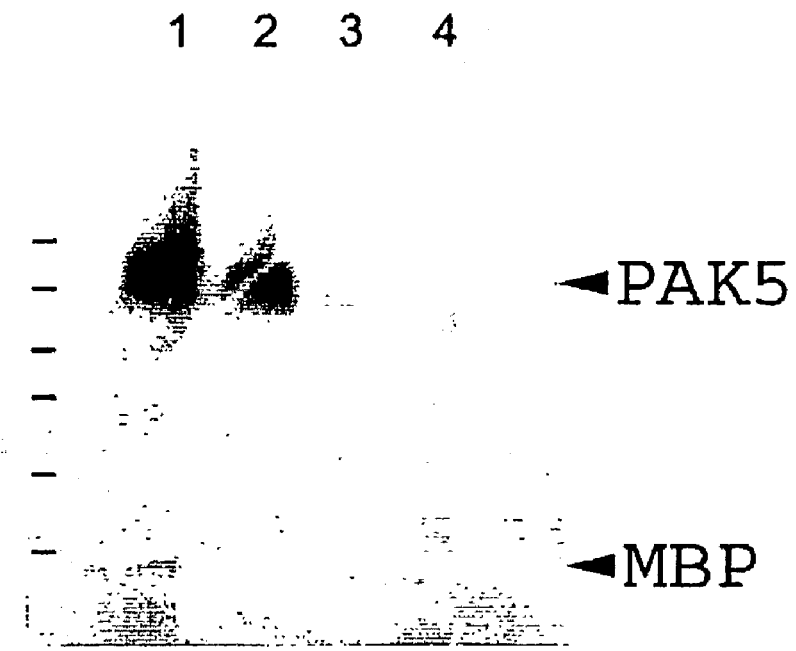
FIG. 1: Kinase assays performed on PAK5 immunopurified from laysate of 293 fibroblasts, showing that this kinase is able to phosphorylate generic substrates.
Figure 1B:
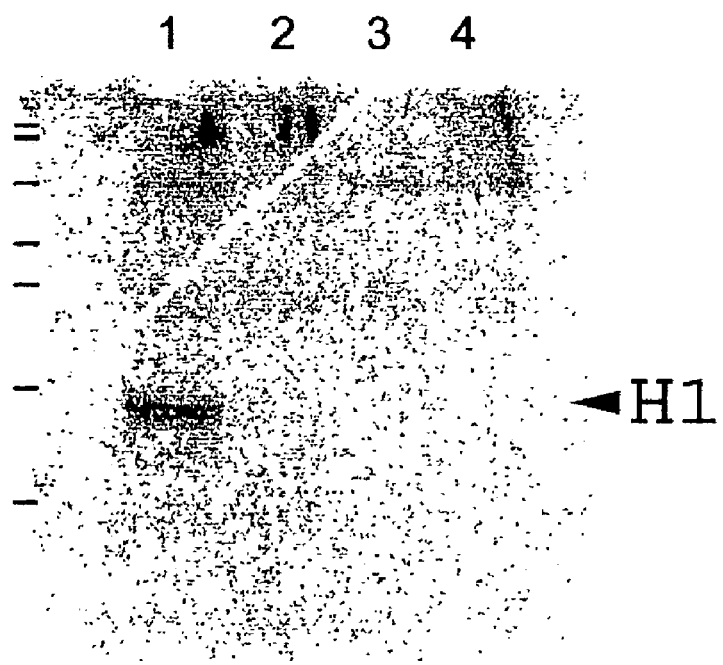

FIG. 1B. Kinase assay performed with histone H1 as substrate. Lanes 1 and 2 correspond to immunoprecipitates from cells transfected with vector encoding PAK5. Lanes 3 and 4 correspond to immunoprecipitates from cells transfected with empty control vector. In lanes 1 and 3, histone H1 was present, in lanes 2 and 4, histone H1 was absent. Bars on the left hand side of the figure indicate the approximate positions of molecular weight markers, the sizes of which, from top to bottom were 120, 80, 50, 35, 27, 20 and 7 kDa.

FIG. 2. Multiple tissue northern blots showing distribution of Pak5 mRNA in normal human tissues.

Figure 2A:
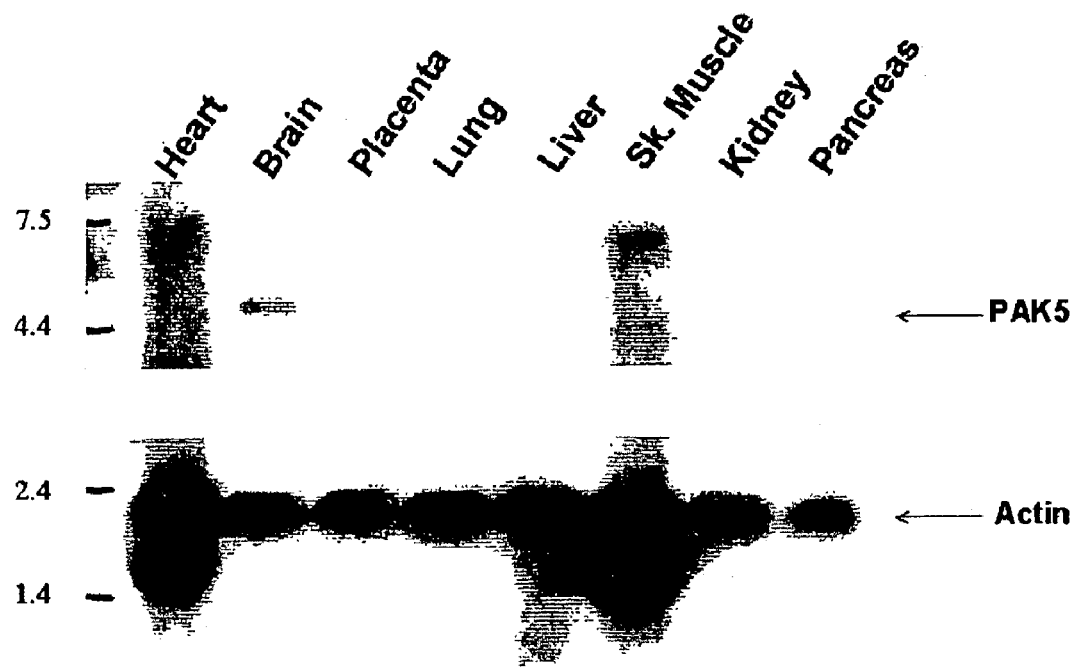

FIG. 2A. Analysis in several distinct tissue types (Clontech human multiple tissue blot #7760-1) shows that PAK5 (upper panel) is expressed selectively in brain. Lower panel shows actin probe supplied with blot as a control.

Figure 2B:
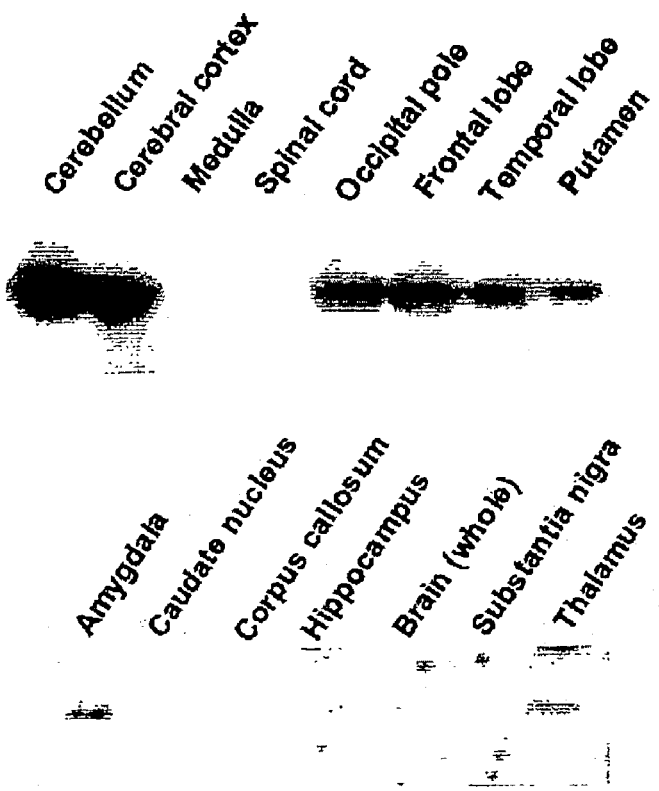

FIG. 2B. Northern analysis of sub-regions of normal human brain shows strong expression in several regions, indicated above the lanes. Upper panel corresponds to Clontech human Brain blot II, #7755-1 and lower panel corresponds to Clontech human Brain blot IV, #7769-1.

EXAMPLES

Example 1

Identification of PAK5

The four known human PAK coding sequences (PAKs 1–4; SEQ ID NO:4, SEQ ID NO:5, SEQ ID NO:6, and SEQ ID NO:7, respectively) were extracted from the GenBank database. The sequences were translated and aligned, the kinase domain regions removed from the alignment, and the remaining non-kinase region alignment was used as input for a hidden Markiv model (HMM) profile generation using WiseTools software (Birney et al., Nucleic Acids Res 24, 2730–2739, 1996). The resulting HMM was used for searching the Incyte EST database. This search yielded an unknown partial sequence of 581 bp (Incyte template 067594.1, SEQ ID NO:8), for which nucleotide residues 352–581 showed significant homology to the first 230 nucleotides of PAK-4 CDS (i.e. SEQ NO:7 residues 1–230). We thus hypothesized that SEQ ID NO:8 represents a partial cDNA clone for a novel member of the PAK family, corresponding to 351 bases of 5' UTR, plus the first 230 bases of coding sequence, with the start codon of the ORF at position 231–233. The ATG at this position forms part of a Kozak consensus sequence for initiation of protein translation (Kozak M, Cell vol. 44: 283–92, 1986). This novel sequence was designated as PAK5 based on the homology to PAK4.

Example 2

Cloning of pak5 cDNA

A sense PCR primer (SEQ ID NO:9) was designed which specifically matches SEQ ID NO:8 at position 347–366, and thus specifically amplifies PAK5, but not the other known PAK family sequences very near to the 5' end of the inferred CDS. An antisense primer near the 3' end of the inferred CDS was designed by aligning the conserved kinase domains located in the 3' region of all PAK protein family members using the Align Program within the VECTOR NTI Suite software (InforMax, Inc., Bethesda, Md.), and choosing by eye a suitable degenerate primer (SEQ ID NO:10) for amplification of the putative PAK5 sequence. This primer has highest homology towards the antisense sequence in position 1438–1457 of the human PAK-4 sequence (SEQ ID NO:7). Thus the primer pair, defined in SEQ ID NO:9 and SEQ ID NO:10, when used in a PCR reaction under suitable conditions, and with suitable template cDNA, should specifically amplify a cDNA fragment encoding most of the novel kinase coding sequence. Standard protocols were used for PCR (see Sambrook, 1987). An MJ Research PTC-225 PCR cycler was used applying 30 cycles of the following conditions: 96° C. for 15 seconds, 54° C. for 15 seconds, 72° C. for 2 minutes. cDNA obtained by reverse transcription of human fetal brain mRNA (Clontech) was used as the template in the PCR reaction. The resulting PCR products were subcloned into the pCR2.1 "TA" vector (Invitrogen) by the TA cloning approach as per kit protocols. The resulting ligation reactions were used to transform INVαF' E. coli competent cells (Invitrogen). Single, isolated transformed E. coli colonies were grown in selective media (LB broth, ampicillin) overnight at 37° C. and subsequently used to prepare plasmid DNA (Qiagen Plasmid DNA preparation kit).

Inserts of two independent clones were sequenced directly using an ABI377 fluorescence-based sequencer (Perkin Elmer/Applied Biosystems Division, PE/ABD, Foster City, Calif.) and the ABI PRISM Ready Dye-Deoxy Terminator kit with Taq FS polymerase. Each ABI cycle sequencing reaction contained about 0.5 µg of plasmid DNA. Cycle-sequencing was performed using an initial denaturation at 98° C. for 1 min, followed by 50 cycles: 98° C. for 30 sec, annealing at 50° C. for 30 sec, and extension at 60° C. for 4 min. Temperature cycles and times were controlled by a Perkin-Elmer 9600 thermocycler. Extension products were purified using Centriflex gel filtration columns (Advanced Genetic Technologies Corp., Gaithersburg, Md.). Each reaction product was loaded by pipette onto the column, which was then centrifuged in a swinging bucket centrifuge (Sorvall model RT6000B tabletop centrifuge) at 1500× g for 4 min at room temperature. Column-purified samples were dried under vacuum for about 40 min and then dissolved in 5 µl of a DNA loading solution (83% deionized formamide, 8.3 mM EDTA, and 1.6 mg/ml Blue Dextran). The samples were then heated to 90° C. for three min and loaded into the gel sample wells for sequence analysis. Sequence analysis was performed by importing ABI377 files into the Sequencher program (Gene Codes, Ann Arbor, Mich.). Generally, sequence reads of 700 bp were obtained. Potential sequencing errors were minimized by obtaining sequence information from both DNA strands and by re-sequencing difficult areas using primers at different locations until all sequencing ambiguities were removed. This resulted in the sequence reported in SEQ ID NO:11. SEQ ID NO:11 was used as a query sequence against the GenBank database. This database was searched for regions of similarity using Gapped BLAST. This resulted in identification of a template sequence, with GenBank ACCESSION #AL31652, having a statistically significant overlapping homology to the query sequence. The sequence identified by template GenBank ACCESSION #AL031652 contains, amongst other, unrelated sequences, a deduced cDNA which encodes the predicted 417 3' terminal residues, including the stop codon (SEQ ID NO:12), of a predicted PAK1-like kinase. The overlapping similarity extended from SEQ ID NO:11 residues 1749 to 1846, compared to template (SEQ ID NO:12) residues 1 to 98, aligning with an overall DNA sequence identity of 98.98%. SEQ ID NO:11 this contained 1748 bp of sequence 5' to the overlap, not present in the public SEQ ID NO:12, while SEQ ID NO:12 contained 319 bp 3' to the overlap, not present in SEQ ID NO:11. Combining this information, it was thus possible to infer the full-length coding sequence for PAK5 by assembling the partial coding sequences contained within SEQ ID NO:8 (i.e. Incyte template 067594.1), SEQ ID NO:11 derived by PCR cloning/sequencing, and SEQ ID NO:12, the deduced partial coding sequence for a "PAK1-like serine threonine kinase" from genomic clone AL031652. Without PCR cloning and sequencing of SEQ ID NO:11, which contains most of the PAK5 sequence, and which was previously unknown, including most of the kinase catalytic domain, it would not have been possible to assign SEQ ID NO:8 and SEQ ID NO:12 as belonging to the same gene. Furthermore, since SEQ ID NO:12 is not an expressed sequence, but is deduced from genomic DNA, with many intervening non-coding sequences (introns), it would not have been possible with the existing information, to deduce that SEQ ID NO:12 is, in fact, expressed as such. When the sequence of SEQ ID NO:11 is assembled together with non-overlapping sequences contained within SEQ ID NO:8 (i.e. Incyte template 067594.1), and those contained within SEQ ID NO:12 (i.e. a deduced partial coding sequence from genomic clone GenBank Accession AL031652), the full-length sequence shown in SEQ. ID. NO:1 is obtained.

In order to formally demonstrate that SEQ ID NO:8, SEQ ID NO:11 and SEQ ID NO:12 do, in fact, represent contiguous stretches of the same gene, the full length PAK5 cDNA was amplified from fetal brain cDAN by PCR using the sense primer described in SEQ ID NO: 13 and antisense primer described in SEQ ID NO:14, which respectively cover the 5' (sense) and 3' (antisense) extremities of the sequence described in SEQ ID NO:1. Several independent clones from independent PCR reactions were sequenced and were found to contain the expected fragment, corresponding to nucleotide residues of SEQ ID NO:1. This sequence contains a 2157 bp (SEQ ID NO:2) major open reading frame (ORF) with a Kozak consensus sequence at the initiation ATG codon. Translation of the ORF resulted in a 719 amino acid protein sequence (SEQ ID NO:3) which has homology with the known PAKs 1–4, and, in particular, contains the conserved GBD/CRIB region and kinase sub-domains found in the PAK family of serine/threonine protein kinases (discussed above). The PAK5 protein has a predicted molecular weight of 80759.01 Dalton, an isoelectric point of 7.72, and a net charge of 3.09 at pH7.0.

Example 3

Assay to Identify Level of PAK5 Kinase Activity

Human 293 cells are transfected with the mammalian expression vector pcDNA3.1 (Invitrogen) encoding full length PAK5, as described in Example 7, or with control (empty vector), and lysed after 24 hours using M-Per mammalian cell lysis buffer (Pierce). 500 $\mu$g of solubilised cellular proteins are diluted to a final volume of 500 $\mu$l with M-Per buffer, and PAK5 is immunoprecipitated by mixing this lysate with 10 $\mu$l Protein A Sepharose (Sigma Chemical Company), and 20 $\mu$l of a polyclonal anti-PAK5 antiserum. Reactions are performed at 4° C. for 2 hours, after which protein A-sepharose pellets containing immunoprecipitates are washed twice by centrifugation (10,000 Xg, 5 minutes) with 500 $\mu$l M-Per buffer, and twice with 500 $\mu$l of modified kinase reaction buffer, containing 20 mM HEPES (pH 7.5), 10 mM magnesium acetate, 1 mM DTT, 0.01 mM sodium orthovanadate. After washing, the 10 $\mu$l Protein A-Sepharose pellets are drained of excess buffer and used for kinase reactions, as described below.

The anti-PAK5 antiserum used for immunoprecipitation is produced by immunisation of rabbits (NZW, Charles River) with a recombinant fusion protein containing GST fused with a fragment of PAK5 corresponding to the PAK5 sequence residues 106 to 404 of SEQ ID NO:3. Immunisation of rabbits and production of antiserum was performed as described in Using Antibodies: A Laboratory Manual by Ed Harlow, David Lane, Cold Spring Harbor Laboratory Press; ISBN:0879695439.

Protein A-sepharose pellets containing immunoprecipitates obtained as described above in a final volume of 10 $\mu$l, are mixed with 20 $\mu$g myelin basic protein (MBP), or with 20 $\mu$g histone H1 (H1) in 10 $\mu$l of a 3X kinase reaction buffer (KRB) containing: 60 mM HEPES (pH 7.5), 30 mM magnesium acetate, 0.15 mM ATP, 3 mM DTT, 0.03 mM sodium orthovanadate. The reaction is started by the addition of 5 $\mu$Ci [γ-32P] ATP (10 $\mu$l). Samples are incubated for 5 minutes at 30° C. and the reaction is stopped by addition of 4X Laemmli sample buffer. Proteins are separated on Tris/glycine SDS gels (pre-made, obtained from Bio-Rad, Richmond, Calif.), stained with Coomassie blue, dried, exposed to phosphoimageing plates (K plates, Bio-Rad, Richmond Calif.), and read on a phosphoimager (Bio-Rad, Richmond Calif.).

FIG. 1 shows the results of such analysis, from which it is clear that PAK5 is able to phosphorylate generic kinase substrates such as myelin basic protein and histone H1.

Example 4

High-Throughput Screening Assay to Identify Compounds that Modulate PAK5 Kinase Activity High throughput screening for modulator compounds can be performed using MBP coated 96-well assay plates ("FLASHPLATES®") (NEN Life ScienceProducts). Kinase reaction buffer (3X kinase reaction buffer (KRB)) contains: 60 mM HEPES (pH 75), 30 mM magnesium acetate, 0.15 mM ATP, 3 mM DTT, 0.03 mM sodium orthovanadate), 0.25 $\mu$Ci [y33P]-ATP at a concentration no greater than 1 $\mu$g/ml, (determined by titration of individual enzyme preparations for a concentration that allows kinetic determinations over a 1 hour time course of the kinase) are added to each well and incubated for 1 hour at 30° C. in the presence or absence of 10 $\mu$M test compound. Total reaction volume is 100 $\mu$l. Following incubation, the reaction mixture is aspirated and the wells rinsed twice with 200 $\mu$l PBS. Incorporation of radiolabeled phosphate is determined by scintillation counting (Packard Instrument Co. TopCount, 12-detector, 96-well microplate scintillation counter and luminescence counter, model B991200). Compounds which inhibit kinase activity >50 percent at 10 $\mu$M are indicated by a >50% reduction in scintillation counts. Specificity and selectivity is determined by titration of inhibitory compounds to determine the IC50 (or other standard quantitation well known in the art for comparison) and by the substitution of other kinases in the assay. For example, determination of the relative inhibitory activity of the kinase in comparison to recombinant PAK4 kinase, expressed and isolated in a similar manner, assayed under similar conditions, provides selectivity data.

Example 5

High-Throughput Screening Assay to Identify Compounds that Modulate PAK5 Activity Test compounds are prepared in advance from 2.5 mg/ml stock solutions in DMSO by diluting 1:10 in distilled water, followed by an additional 1:10 dilution in water. 10 μl of the 1:100 dilution solutions (25 μg/ml in 1% DMSO) are prepared in 96 well Microlite 1 plates (Dynex) and plates are stored at −20° C. until the evening prior to the start of the assay.

The signal from wells containing test compounds is compared to zero inhibition wells containing 10 μl of 1% (v/v) DMSO solution in MilliQ water, and to 100% inhibition wells containing 10 μl of 200 mM EDTA in 1% DMSO solution in MilliQ water. 50% inhibition wells contain a reference compound at a concentration known to provide approximately 50% inhibition in 1% (v/v) DMSO solution in MilliQ water.

Assay components (1) recombinant Pak5 kinase (expressed in *E. coli* or eukaryotic cells as described herein) or a lysate of a prokaryotic or eukaryotic cell expressing recombinant enzyme, or the natural enzyme partially purified from a human cell line.

(2) [γ33-P]-adenosine triphosphate in 3X KRB (3) myelin basic protein linked to the surface of PVT SPA (Scintillation Proximity Assay) beads (purchased from Amersham Pharmacia Biotech) by an antibody-protein A or other appropriate method.

To Microlite 1 plates containing 10 μl of test compound, which were left on the bench overnight to reach room temperature, 20 μl of ATP/ATP$_{33}$ is added, immediately followed by 30 μl of Enzyme, using two Multidrops. The plates are stacked (with an empty plate on top of each stack to minimize evaporation from the top plate) and left at room temperature for 105 minutes. 150 μl of "Stop Solution" containing anti-beads antibody and EDTA is added using a Multidrop. The plates are sealed with plate sealers and left on the bench overnight, surrounded by perspex screens. The plates are then contrifuged (Heraeus Megafuge 3.0R) at 2500 rpm for 5 minutes and counted on a Topcount instrument; (isotope: $P^{33}$, counting time: 20 seconds/well). A threshold for inhibition is set, e.g., 60% inhibition of scintillation signal. Compounds reaching the inhibition threshold are scored as active.

Example 6

Northern Blot Analysis

Northern blots were performed to examine the expression of mRNA. Sense and antisense primers are selected based on the PAK5 sequence set forth, as SEQ ID NO: 2. A fragment from positions 318–1212 of SEQ ID NO:2 was amplified and used as a probe.

Multiple human tissue northern blot from Clontech (Human MTN #7760-1) were hybridized with the probe. Prehybridization was carried out at 42° C. for 4 hours in 5×SSC, 1×Denhardt's reagent, 0.1% SDS, 50% formamide, 250 mg/ml salmon sperm DNA. Hybridization was performed overnight at 42° C. in the same mixture with the addition of about 1.5×10⁶ cpm/ml of labelled probe.

The probe was labelled with γ-32P-dCTP by Rediprime DNA labelling system (Amersham Pharmacia), purified on Nick Column (Amersham, Pharmacia) and added to the hybridization solution. The filters were washed several times at 42° C. in 0.2× SSC, 0.1% SDS. Filters were exposed to phosphoimageing plates (K plates, Bio-Rad, Richmond Calif.), and read on a phosphoimager (Bio-Rad, Richmond Calif.).

The results of such analysis is shown in FIG. 2A. Using PAK5 probe, a single approximately 5 kb mRNA is detected in brain (FIG. 2A, upper panel). Equal loading of all the lanes was verified by filter hybridisation with a human actin probe (FIG. 2A, lower panel).

In order to further investigate the distribution of PAK5 in normal human brain, the Northern blotting procedure described above was repeated using Clontech brain subregion blots (Clontech Human MTN Brain II, #7755-1, and Human MTN Brain IV, 190 7769-1). The result of this analysis is shown in FIG. 2B. PAK5 is particularly strongly expressed in cerebellum, cerebral cortex, occipital pole and frontal lobe, but can be readily detected in most other region of the brain.

Example 7

Expression of PAK5 in Mammalian Cells

1. Expression of PAK5 in 293 cells

For expression of PAK5 in mammalian cells 293 (transformed human, primary embryonic kidney cells), a plasmid bearing the relevant PAK5 coding sequence is prepared, using vector pcDNA3.1 myc-his (Invitrogen). The plasmid contains nucleotides 1 through 2157 of SEQ ID NO:2. Vector pcDNA3.1 contains the c-myc epitope for detection of the recombinant protein with the anti-myc antibody, a C-terminal polyhistidine for purification with nickel chelate chromatography, and a Neomycin resistant gene for selection of stable transfectants. The forward primer for amplification of PAK5 cDNA is selected using methods available to one of skill in the art based on the sequence of SEQ ID NO:2 and including a 5' extension of 19 nucleotides to introduce the NotI cloning site and 22 nucleotides matching the PAK5 sequence. The reverse primer is selected using methods available to one of skill in the art based on the sequence of SEQ ID NO: 2 and which contains a 5' extension of 8 nucleotides to introduce a BamH1 restriction site for cloning and 17 nucleotides corresponding to the reverse complement of the PAK5 sequence. The PCR conditions are 55oC as the annealing temperature. The PCR product is gel purified and cloned into the NotI-BamH1 sites of the vector.

The DNA is purified using Qiagen chromatography columns and transfected into 293 cells using SUPERFACT transfection media (Qiagen). Transiently transfected cells are tested for expression after 24 hours of transfection, using Western blots probed with anti-His and anti-PAK5 peptide antibodies. Permanently transfected cells are selected with G418 and propagated. Production of the recombinant protein is detected from cells by Western blots probed with anti-His, anti-Myc or anti-PAK5 peptide antibodies.

For expression of a fragment lacking the kinase region of PAK5, a plasmid comprising nucleotides 1–1347 is generated, following the procedure set forth above.

For expression of a fragment containing the kinase domain of PAK5, a plasmid comprising nucleotides 1318–2157 is generated.

2. Expression of PAK5 in COS cells

For expression of PAK5 in COS7 cells, a polynucleotide molecule having the sequence given of SEQ ID NO:2 is cloned into vector pSecTag2A. Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants.

The forward primer for amplification of PAK5 cDNA is selected using methods available to one of skill in the art based on the sequence of SEQ ID NO: 2 and including a 5' extension of 19 nucleotides to introduce the HindIII restriction site for cloning and 22 nucleotides matching the PAK5 sequence given in SEQ ID NO: 2. The reverse primer is selected using methods available to one of skill in the art based on the sequence of SEQ ID NO: 2 and which contains a 5' extension of 8 nucleotides to introduce a BamH1 restriction site for cloning and 17 nucleotides corresponding to the reverse complement of the PAK5 sequence given in SEQ ID NO: 2. The PCR consists of an initial denaturation step of 5 min at 95 C, 30 cycles of 30 sec denaturation at 95 C, 30 sec annealing at 58 C and 30 sec extension at 72 C, followed by 5 min extension at 72 C. The PCR product is gel purified and ligated into the XbaI and SalI sites of vector p3-CI. This construct is transformed into *E. coli* cells for amplification and DNA purification. The DNA is purified with Qiagen chromatography columns and transfected into COS 7 cells using Lipofectamine reagent from BRL, following the manufacturer's protocols. Forty-eight and 72 hours after transfection, the media and the cells are tested for recombinant protein expression.

PAK5 expressed from a COS cell culture can be purified by concentrating the cell-growth media to about 10 mg of protein/ml, and purifying the protein by, for example, chromatography. Purified PAK5 is concentrated to 0.5 mg/ml in an Amicon concentrator fitted with a YM-10 membrane and stored at –80oC.

Example 8

Expression of PAK5 in Insect Cells

For expression of PAK5 in a baculovirus system, a polynucleotide molecule having the sequence given as SEQ ID NO:2 was amplified by PCR. The forward primer first consists of a 5' extension which adds the NotI cloning site, followed by 22 nucleotides which correspond to nucleotide of the sequence given in SEQ ID NO:2. The reverse primer first comprises a 5' extension which introduces the BamH1 cloning site, followed by followed by 17 nucleotides which correspond to the reverse complement of nucleotides given in SEQ ID NO:2.

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the *Autographa california* nuclear polyhedrosis virus (AcMNPV), and a 6XHis tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of PAK5 polypeptides can be used, provided that the vector construct includes appropriately located signals for transcription, translation, and trafficking, such as an in-frame AUG and a signal peptide, as required. Such vectors are described in Luckow et al., *Virology* 170:31–39, among others.

The virus is grown and isolated using standard baculovirus expression methods, such as those described in Summers et al. (A Manual of Methods for Baculovirus Vectors and Insect Cell Culture Procedures, Texas Agricultural Experimental Station Bulletin No. 1555 (1987)).

In a preferred embodiment, pAcHLT-A containing the PAK5 gene is introduced into baculovirus using the "BaculoGold" transfection kit (Pharmingen, San Diego, Calif.) using methods established by the manufacturer. Individual virus isolates are analyzed for protein production by radiolabeling infected cells with 35S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of the PAK5 polypeptide in a Sf9 cells, a polynucleotide molecule having the sequence given in SEQ ID NO:2 is amplified by PCR using the primers and methods described above for baculovirus expression. The PAK5 cDNA is cloned into vector pAcHLT-A (Pharmingen) for expression in Sf9 insect. The insert is cloned into the NotI and BamH1 sites, after elimination of an internal NdeI site (using the same primers described above for expression in baculovirus). DNA is purified with Qiagen chromatography columns and expressed in Sf9 cells. Preliminary Western blot experiments from non-purified plaques are tested for the presence of the recombinant protein of the expected size which reacted with the PAK5-specific antibody. These results are confirmed after further purification and expression optimization in HiG5 cells.

Example 9

Interaction Trap/Two-Hybrid System

In order to assay for PAK5-interacting proteins, the interaction trap/two-hybrid library screening method can be used. This assay was first described in Fields et al., *Nature*, 1989, 340, 245, which is incorporated herein by reference in its entirety. A protocol is published in *Current Protocols in Molecular Biology* 1999, John Wiley & Sons, NY and Ausubel, F. M. et al. 1992, *Short protocols in molecular biology*, Fourth edition, Greene and Wiley-Interscience, NY, which is incorporated herein by reference in its entirety. Kits are available from Clontech, Palo Alto, Calif. (Matchmaker Two-Hybrid System 3).

A fusion of the nucleotide sequences encoding all or partial PAK5 and the yeast transcription factor GAL4 DNA-binding domain (DNA-BD) is constructed in an appropriate plasmid (i.e. pGBKT7) using standard subcloning techniques. Similarly, a GAL4 active domain (AD) fusion library is constructed in a second plasmid (i.e. pGADT7) from cDNA of potential PAK-5-binding proteins (for protocols on forming cDNA libraries, see Sammbrook et al. 1989, *Molecular cloning: a laboratory manual*, second edition, Cold Spring Harbor Press, Cold Spring Harbor, N.Y.), which is incorporated herein by reference in its entirety. The DNA-BD/PAK5 fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. $10^5$ transformants/mg DNA) with both the PAK5 and library fusion plasmids according to standard procedure (Ausubel, et al., 1992, *Short protocols in molecular biology*, Fourth edition, Greene and Wiley-Intersicence, NY, which is incorporated herein by reference in its entirety). In vivo binding of DNA-BD/PAK5 with AD/library proteins results in transcription of specific yeast plasmid reporter genes (ie. lacZ, HIS3, ADE2, LEU2). Yeast cells are plated on nutrient-deficient media to screen for expression of reporter genes. Colonies are dually assayed for ⊒-galactosidase activity upon growth in Xgal (5-bromo-4-chloro-3-indoly-⊒-D-galactoside) supplemented media (filter assay for ⊒-galactosidase activity is described in Breeden et al., *Cold Spring Harb. Symp. Quant. Biol.*, 1985, 50, 643, which is incorporated herein by reference in its entirety). Positive AD-library plasmids are rescued from transformants and reintroduced into the original yeast strain as well as other strains containing unrelated DNA-BD fusion proteins to confirm specific PAK5/library protein interactions. Insert DNA is sequenced to verify the presence of an open reading frame fused to GAL4 AD and to determine the identity of the PAK5.

Example 10

Mobility Shift DNA-Binding Assay Using Gel Electrophoresis

A gel electrophoresis mobility shift assay can rapidly detect specific protein-DNA interactions. Protocols are widely available in such manuals as Sambrook et al. 1989, *Molecular cloning: a laboratory manual*, second edition, Cold Spring Harbor Press, Cold Spring Harbor, N.Y. and Ausubel, F. M. et al. 1992, *Short protocols in molecular biology*, Fourth edition, Greene and Wiley-Interscience, NY, each of which is incorporated herein by reference in its entirety.

Probe DNA(<300 bp) is obtained from synthetic oligonucleotides, restriction endonuclease fragments, or PCR fragments and end-labeled with $^{32}$P. An aliquot of purified PAK5 (ca. 15 μg) or crude PAK5 extract (ca. 15 ng) is incubated at constant temperature (in the range 22–37 C) for at least 30 minutes in 10–15 μl of buffer (i.e., TAE or TBE, pH 8.0–8.5) containing radiolabeled probe DNA, nonspecific carrier DNA (ca. 1 μg), BSA (300 μg/ml), and 10% (v/v) glycerol. The reaction mixture is then loaded onto a polyacrylamide gel and run at 30–35 mA until good separation of free probe DNA from protein-DNA complexes occurs. The gel is then dried and bands corresponding to free DNA and protein-DNA complexes are detected by autoradiography.

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:

1. A purified or isolated polypeptide that comprises the amino acid sequence set forth in SEQ ID NO:3.

* * * * *

SEQUENCE LISTING

```
<160> NUMBER OF SEQ ID NOS: 20

<210> SEQ ID NO 1
<211> LENGTH: 2511
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N is any Nucleotide

<400> SEQUENCE: 1
gagaccggga acatggcgct gggagcnctg tagcagctga gaagggctg aggcaccgcc      60 gcttcgctga cagccggcca ccagatgttc atgcattcta gagaaagtgg aaaacttaga    120
agcctaatta atgactgtct tctggacctc tgagaccatg tttctagtgt tttccgtgga    180
atattatcag aaatacactg tggtgaaatg cttccacctc ttgctaaaat gaacactgag    240
gaaaaatgaa gaagactgac aagcaccagc gaaaagttgc agaatagaaa tagccacact    300
cctctggagt ctttaattca tccacagcca tcatataaag gttttggcat catgtttggg    360
aagaaaaaga aaaagattga aatatctggc ccgtccaact ttgaacacag ggttcatact    420
gggtttgatc cacaagagca gaagtttacc ggccttcccc agcagtggca cagcctgtta    480
gcagatacgg ccaacaggcc aaagcctatg gtggaccctt catgcatcac acccatccag    540
ctggctccta tgaagacaat cgttagagga aacaaaccct gcaaggaaac ctccatcaac    600
ggcctgctag aggattttga caacatctcg gtgactcgct ccaactccct aaggaaagaa    660
```

-continued

```
agcccaccca ccccagatca gggagcctcc agccacggtc caggccacgc ggaagaaaat      720
ggcttcatca ccttctccca gtattccagc gaatccgata ctactgctga ctacacgacc      780
gaaaagtaca gggagaagag tctctatgga gatgatctgg atccgtatta tagaggcagc      840
cacgcagcca agcaaaatgg gcacgtaatg aaaatgaagc acggggaggc ctactattct      900
gaggtgaagc cttgaaatc cgattttgcc agattttctg ccgattatca ctcacatttg      960
gactcactga gcaaaccaag tgaatacagt gacctcaagt gggagtatca gagagcctcg     1020
agtagctccc ctctggatta ttcattccaa ttcacacctt ctagaactgc agggaccagc     1080
gggtgctcca aggagagcct ggcgtacagt gaaagtgaat ggggacccag cctggatgac     1140
tatgacagga ggccaaagtc ttcgtacctg aatcagacaa gccctcagcc caccatgcgg     1200
cagaggtcca ggtcaggctc gggactccag gaaccgatga tgccatttgg agcaagtgca     1260
tttaaaaccc atccccaagg acactcctac aactcctaca cctaccctcg cttgtccgag     1320
cccacaatgt gcattccaaa ggtggattac gatcgagcac agatggtcct cagccctcca     1380
ctgtcagggt ctgacaccta ccccagggc cctgccaaac tacctcaaag tcaaagcaaa      1440
tcgggctatt cctcaagcag tcaccagtac ccgtctgggt accacaaagc caccttgtac     1500
catcacccct ccctgcagag cagttcgcag tacatctcca cggcttccta cctgagctcc     1560
ctcagcctct catccagcac ctaccgccg cccagctggg gctcctcctc cgaccagcag      1620
ccctccaggg tgtcccatga acagtttcgg gcggccctgc agctggtggt cagcccagga     1680
gaccccaggg aatacttggc caactttatc aaaatcgggg aaggctcaac cggcatcgta     1740
tgcatcggca ccgagaaaca cagggaaa caagttgcag tgaagaaaat ggacctccgg       1800
aagcaacaga gacgagaact gctttttcaat gaggtcgtga tcatgcggga ttaccaccat    1860
gacaatgtgg ttgacatgta cagcagctac cttgtcggcg atgagctctg ggtggtcatg     1920
gagtttctag aaggtggtgc cttgacagac attgtgactc acaccagaat gaatgaagaa     1980
cagatagcta ctgtctgcct gtcagttctg agagctctct cctaccttca taaccaagga    2040
gtgattcaca gggacataaa agtgactcc atcctcctga caagcgatgg ccggataaag      2100
ttgtctgatt ttggttctg tgctcaagtt tccaaagagg tgccgaagag gaaatcattg      2160
gttggcactc cctactggat ggcccctgag ctgatttcta ggctaccta tgggacagag      2220 gtggacatct ggtccctcgg gatcatggtg atagaaatga ttgatggcga ccccctac      2280 ttcaatgagc ctccctcca ggcgatgcgg aggatccggg acagtttacc tccaagagtg     2340
aaggacctac acaaggtttc ttcagtgctc cggggattcc tagacttgat gttggtgagg     2400
gagccctctc agagagcaac agcccaggaa ctcctcggac atccattctt aaaactagca    2460
ggtccaccgt cttgcatcgt cccctcatg agacaataca ggcatcactg a              2511
```

<210> SEQ ID NO 2
<211> LENGTH: 2157
<212> TYPE: DNA
<213> ORGANISM: Homo sapiens

<400> SEQUENCE: 2

```
atgtttggga agaaaaagaa aaagattgaa atatctggcc cgtccaactt tgaacacagg       60
gttcatactg ggtttgatcc acaagagcag aagtttaccg gccttcccca gcagtggcac      120
agcctgttag cagatacggc caacaggcca agcctatgg tggacccttc atgcatcaca       180
cccatccagc tggctcctat gaagacaatc gttagaggaa acaaacctg caaggaaacc       240
```

-continued

```
tccatcaacg gcctgctaga ggattttgac aacatctcgg tgactcgctc caactcccta      300
aggaaagaaa gcccacccac cccagatcag ggagcctcca gccacggtcc aggccacgcg      360
gaagaaaatg gcttcatcac cttctcccag tattccagcg aatccgatac tactgctgac      420
tacacgaccg aaaagtacag ggagaagagt ctctatggag atgatctgga tccgtattat      480
agaggcagcc acgcagccaa gcaaaatggg cacgtaatga aaatgaagca cggggaggcc      540
tactattctg aggtgaagcc tttgaaatcc gattttgcca gattttctgc cgattatcac      600
tcacatttgg actcactgag caaaccaagt gaatacagtg acctcaagtg ggagtatcag      660
agagcctcga gtagctcccc tctggattat tcattccaat tcacaccttc tagaactgca      720
gggaccagcg ggtgctccaa ggagagcctg gcgtacagtg aaagtgaatg gggacccagc      780
ctggatgact atgacaggag gccaaagtct tcgtacctga atcagacaag ccctcagccc      840
accatgcggc agaggtccag gtcaggctcg ggactccagg aaccgatgat gccatttgga      900
gcaagtgcat ttaaaaccca tccccaagga cactcctaca actcctacac ctaccctcgc      960
ttgtccgagc ccacaatgtg cattccaaag gtggattacg atcgagcaca gatggtcctc     1020
agccctccac tgtcagggtc tgacacctac cccaggggcc ctgccaaact acctcaaagt     1080
caaagcaaat cgggctattc ctcaagcagt caccagtacc cgtctgggta ccacaaagcc     1140
accttgtacc atcacccctc cctgcagagc agttcgcagt acatctccac ggcttcctac     1200
ctgagctccc tcagcctctc atccagcacc tacccgccgc ccagctgggg ctcctcctcc     1260
gaccagcagc cctccagggt gtcccatgaa cagtttcggg cggccctgca gctggtggtc     1320
agcccaggag accccaggga atacttggcc aactttatca aaatcgggga aggctcaacc     1380
ggcatcgtat gcatcggcac cgagaaacac acagggaaac aagttgcagt gaagaaaatg     1440
gacctccgga agcaacagag acgagaactg cttttcaatg aggtcgtgat catgcgggat     1500
taccaccatg acaatgtggt tgacatgtac agcagctacc ttgtcggcga tgagctctgg     1560
gtggtcatgg agtttctaga aggtggtgcc ttgacagaca ttgtgactca caccagaatg     1620
aatgaagaac agatagctac tgtctgcctg tcagttctga gagctctctc ctaccttcat     1680
aaccaaggag tgattcacag ggacataaaa agtgactcca tcctcctgac aagcgatggc     1740
cggataaagt tgtctgattt tggtttctgt gctcaagttt ccaaagaggt gccgaagagg     1800
aaatcattgg ttggcactcc ctactggatg gcccctgagc tgatttctag gctaccttat     1860
gggacagagg tggacatctg gtccctcggg atcatggtga tagaaatgat tgatggcgag     1920 ccccccctact tcaatgagcc tcccctccag gcgatgcgga ggatccggga cagtttacct     1980
ccaagagtga aggacctaca caaggttttct tcagtgctcc ggggattcct agacttgatg     2040
ttggtgaggg agccctctca gagagcaaca gcccaggaac tcctcggaca tccattctta     2100
aaactagcag gtccaccgtc ttgcatcgtc cccctcatga gacaatacag gcatcac        2157
```

<210> SEQ ID NO 3
<211> LENGTH: 719
<212> TYPE: PRT
<213> ORGANISM: Homo sapiens

<400> SEQUENCE: 3

```
Met Phe Gly Lys Lys Lys Lys Ile Glu Ile Ser Gly Pro Ser Asn
 1               5                  10                  15

Phe Glu His Arg Val His Thr Gly Phe Asp Pro Gln Glu Gln Lys Phe
                20                  25                  30

Thr Gly Leu Pro Gln Gln Trp His Ser Leu Leu Ala Asp Thr Ala Asn
```

-continued

```
                35                  40                  45
Arg Pro Lys Pro Met Val Asp Pro Ser Cys Ile Thr Pro Ile Gln Leu
 50                  55                  60

Ala Pro Met Lys Thr Ile Val Arg Gly Asn Lys Pro Cys Lys Glu Thr
 65                  70                  75                  80

Ser Ile Asn Gly Leu Leu Glu Asp Phe Asp Asn Ile Ser Val Thr Arg
                 85                  90                  95

Ser Asn Ser Leu Arg Lys Glu Ser Pro Thr Pro Asp Gln Gly Ala
                100                 105                 110

Ser Ser His Gly Pro Gly His Ala Glu Glu Asn Gly Phe Ile Thr Phe
                115                 120                 125

Ser Gln Tyr Ser Ser Glu Ser Asp Thr Thr Ala Asp Tyr Thr Thr Glu
                130                 135                 140

Lys Tyr Arg Glu Lys Ser Leu Tyr Gly Asp Asp Leu Asp Pro Tyr Tyr
145                 150                 155                 160

Arg Gly Ser His Ala Ala Lys Gln Asn Gly His Val Met Lys Met Lys
                165                 170                 175

His Gly Glu Ala Tyr Tyr Ser Glu Val Lys Pro Leu Lys Ser Asp Phe
                180                 185                 190

Ala Arg Phe Ser Ala Asp Tyr His Ser His Leu Asp Ser Leu Ser Lys
                195                 200                 205

Pro Ser Glu Tyr Ser Asp Leu Lys Trp Glu Tyr Gln Arg Ala Ser Ser
                210                 215                 220

Ser Ser Pro Leu Asp Tyr Ser Phe Gln Phe Thr Pro Ser Arg Thr Ala
225                 230                 235                 240

Gly Thr Ser Gly Cys Ser Lys Glu Ser Leu Ala Tyr Ser Glu Ser Glu
                245                 250                 255

Trp Gly Pro Ser Leu Asp Asp Tyr Asp Arg Arg Pro Lys Ser Ser Tyr
                260                 265                 270

Leu Asn Gln Thr Ser Pro Gln Pro Thr Met Arg Gln Arg Ser Arg Ser
                275                 280                 285

Gly Ser Gly Leu Gln Glu Pro Met Met Pro Phe Gly Ala Ser Ala Phe
                290                 295                 300

Lys Thr His Pro Gln Gly His Ser Tyr Asn Ser Tyr Thr Tyr Pro Arg
305                 310                 315                 320

Leu Ser Glu Pro Thr Met Cys Ile Pro Lys Val Asp Tyr Asp Arg Ala
                325                 330                 335

Gln Met Val Leu Ser Pro Pro Leu Ser Gly Ser Asp Thr Tyr Pro Arg
                340                 345                 350

Gly Pro Ala Lys Leu Pro Gln Ser Gln Ser Lys Ser Gly Tyr Ser Ser
                355                 360                 365

Ser Ser His Gln Tyr Pro Ser Gly Tyr His Lys Ala Thr Leu Tyr His
                370                 375                 380

His Pro Ser Leu Gln Ser Ser Gln Tyr Ile Ser Thr Ala Ser Tyr
385                 390                 395                 400

Leu Ser Ser Leu Ser Leu Ser Ser Thr Tyr Pro Pro Ser Trp
                405                 410                 415

Gly Ser Ser Asp Gln Gln Pro Ser Arg Val Ser His Glu Gln Phe
                420                 425                 430

Arg Ala Ala Leu Gln Leu Val Val Ser Pro Gly Asp Pro Arg Glu Tyr
                435                 440                 445

Leu Ala Asn Phe Ile Lys Ile Gly Glu Gly Ser Thr Gly Ile Val Cys
450                 455                 460
```

```
Ile Gly Thr Glu Lys His Thr Gly Lys Gln Val Ala Val Lys Lys Met
465                 470                 475                 480

Asp Leu Arg Lys Gln Gln Arg Arg Glu Leu Leu Phe Asn Glu Val Val
            485                 490                 495

Ile Met Arg Asp Tyr His His Asp Asn Val Val Asp Met Tyr Ser Ser
        500                 505                 510

Tyr Leu Val Gly Asp Glu Leu Trp Val Val Met Glu Phe Leu Glu Gly
    515                 520                 525

Gly Ala Leu Thr Asp Ile Val Thr His Thr Arg Met Asn Glu Glu Gln
530                 535                 540

Ile Ala Thr Val Cys Leu Ser Val Leu Arg Ala Leu Ser Tyr Leu His
545                 550                 555                 560

Asn Gln Gly Val Ile His Arg Asp Ile Lys Ser Asp Ser Ile Leu Leu
                565                 570                 575

Thr Ser Asp Gly Arg Ile Lys Leu Ser Asp Phe Gly Phe Cys Ala Gln
            580                 585                 590

Val Ser Lys Glu Val Pro Lys Arg Lys Ser Leu Val Gly Thr Pro Tyr
        595                 600                 605

Trp Met Ala Pro Glu Leu Ile Ser Arg Leu Pro Tyr Gly Thr Glu Val
    610                 615                 620

Asp Ile Trp Ser Leu Gly Ile Met Val Ile Glu Met Ile Asp Gly Glu
625                 630                 635                 640

Pro Pro Tyr Phe Asn Glu Pro Pro Leu Gln Ala Met Arg Arg Ile Arg
                645                 650                 655

Asp Ser Leu Pro Pro Arg Val Lys Asp Leu His Lys Val Ser Ser Val
            660                 665                 670

Leu Arg Gly Phe Leu Asp Leu Met Leu Val Arg Glu Pro Ser Gln Arg
        675                 680                 685

Ala Thr Ala Gln Glu Leu Leu Gly His Pro Phe Leu Lys Leu Ala Gly
    690                 695                 700

Pro Pro Ser Cys Ile Val Pro Leu Met Arg Gln Tyr Arg His His
705                 710                 715

<210> SEQ ID NO 4
<211> LENGTH: 1638
<212> TYPE: DNA
<213> ORGANISM: Homo sapiens

<400> SEQUENCE: 4
atgtcaaata acggcctaga cattcaagac aaaccccag  cccctccgat gagaaatacc      60
agcactatga ttggagccgg cagcaaagat gctggaaccc taaccatgg  ttctaaacct     120 ctgcctccaa acccagagga agagaaaaag aaggaccgat tttaccgatc cattttacct     180
ggagataaaa caaataaaaa gaaagagaaa gagcggccag agatttctct cccttcagat     240
tttgaacaca caattcatgt cggttttgat gctgtcacag gggagtttac cggaatgcca     300
gagcagtggg cccgcttgct tcagacatca aatatcacta gtcggagca  aagaaaaac      360 ccgcaggctg ttctggatgt gttggagttt acaactcga  agaagacatc caacagccag     420
aaatacatga gctttacaga taagtcagct gaggattaca attcttctaa tgccttgaat     480
gtgaaggctg tgtctgagac tcctgcagtg ccaccagttt cagaagatga ggatgatgat     540
gatgatgatg ctaccccacc accagtgatt gctccacgcc agagcacac  aaaatctgta     600 tacacacggt ctgtgattga accacttcct gtcactccaa ctcgggacgt ggctacatct     660
```

-continued

```
cccatttcac ctactgaaaa taacaccact ccaccagatg ctttgacccct taatactgag      720 aagcagaaga agaagcctaa aatgtctgat gaggagatct tggagaaatt acgaagcata      780
gtgagtgtgg gcgatcctaa gaagaaatat acacggtttg agaagattgg acaaggtgct      840
tcaggcaccg tgtacacagc aatggatgtg gccacaggac aggaggtggc cattaagcag      900
atgaatcttc agcagcagcc caagaaagag ctgattatta atgagatcct ggtcatgagg      960
gaaaacaaga acccaaacat tgtgaattac ttggacagtt acctcgtggg agatgagctg     1020
tgggttgtta tggaatactt ggctggaggc tccttgacag atgtggtgac agaaacttgc     1080
atggatgaag gccaaattgc agctgtgtgc cgtgagtgtc tgcaggctct ggagtctttg     1140
cattcgaacc aggtcattca cagagacatc aagagtgaca atattctgtt gggaatggat     1200
ggctctgtca agctaactga ctttggattc tgtgcacaga taaccccaga gcagagcaaa     1260
cggagcacca tggtaggaac cccatactgg atggcaccag aggttgtgac acgaaaggcc     1320
tatgggccca aggttgacat ctggtccctg ggcatcatgg ccatcgaaat gattgaaggg     1380
gagcctccat acctcaatga aaaccctctg agagccttgt acctcattgc caccaatggg     1440
accccagaac ttcagaaccc agagaagctg tcagctatct tccgggactt tctgaaccgc     1500
tgtctcgaga tggatgtgga aagagaggt tcagctaaag agctgctaca gcatcaattc     1560
ctgaagattg ccaagccct ctccagcctc actccactga ttgctgcagc taaggaggca     1620
acaaagaaca atcactaa                                                  1638
```

<210> SEQ ID NO 5
<211> LENGTH: 1578
<212> TYPE: DNA
<213> ORGANISM: Homo sapiens

<400> SEQUENCE: 5

```
atgtctgata acggagaact ggaagataag cctccagcac ctcctgtgcg aatgagcagc       60
accatcttta gcactggagg caaagaccct ttgtcagcca atcacagttt gaaacctttg      120
ccctctgttc cagaagagaa aaagcccagg cataaaatca tctccatatt ctcaggcaca      180
gagaaaggaa gtaaaagaa agaaaaggaa cggccagaaa tttctcctcc atctgatttt      240
gagcacacca tccatgttgg ctttgatgct gttactggag aattcactgg catgccagaa      300
cagtgggctc gattactaca gacctccaat atcaccaaac tagagcaaaa gaagaatcct      360
caggctgtgc tggatgtcct aaagttctac gactccaaca cagtgaagca gaaatatctg      420
agctttactc ctcctgagaa agatggcctt ccttctggaa cgccagcact gaatgccaag      480
ggaacagaag cacccgcagt agtgacagag gaggaggatg atgatgaaga gactgctcct      540
cccgttattg ccccgcgacc ggatcatacg aaatcaattt acacacggtc tgtaattgac      600
cctgttcctg caccagttgg tgattcacat gttgatggtg ctgccaagtc tttagacaaa      660
cagaaaaaga agcctaagat gacagatgaa gagattatg agaaattaag aactatcgtg      720
agcataggtg accctaagaa aaatataca agatatgaaa aaattggaca agggcttct      780 ggtacagttt tcactgctac tgacgttgca ctgggacagg aggttgctat caaacaaatt      840
aatttacaga aacagccaaa gaaggaactg atcattaacg agattctggt gatgaaagaa      900
ttgaaaaatc ccaacatcgt taacttttg gacagttacc tggtaggaga tgaattgttt      960
gtggtcatgg aataccttgc tgggggtgca ctcactgatg tggtaacaga aacagcttgc     1020
atggatgaag cacagattgc tgctgtatgc agagagtgtt tacaggcatt ggagtttta    1080 catgctaatc aagtgatcca cagagacatc aaaagtgaca atgtacttt ggggaatggaa     1140
```

-continued

```
ggatctgtta agctcactga ctttggtttc tgtgcccaga tcacccctga gcagagcaaa    1200
cgcagtacca tggtcggaac gccatactgg atggcaccag aggtggttac acggaaagct    1260
tatggcccta aagtcgacat atggtctctg gtatcatgg ctattgagat ggtagaagga     1320
gagcctccat acctcaatga aaatcccttg agggccttgt acctaatagc aactaatgga    1380
accccagaac ttcagaatcc agagaaactt tccccaatat ttcgggattt cttaaatcga    1440
tgtttggaaa tggatgtgga aaaagggggt tcagccaaag aattattaca gcatccttc     1500 ctgaaactgg ccaaaccgtt atctagcttg acaccactga tcatggcagc taaagaagca    1560
atgaagagta accgttaa                                                  1578
```

<210> SEQ ID NO 6
<211> LENGTH: 1635
<212> TYPE: DNA
<213> ORGANISM: Homo sapiens

<400> SEQUENCE: 6

```
atgtctgacg gtctggataa tgaagagaaa cccccggctc ctccactgag gatgaatagt     60
aacaaccggg attcttcagc actcaaccac agctccaaac cacttcccat ggcccctgaa    120
gagaagaata gaaagccag gcttcgctct atcttcccag gaggaggga taaaaccaat     180 aagaagaagg agaaagagcg cccagagatc tctcttcctt cagactttga gcatacgatt    240
catgtggggt ttgatgcagt caccggggaa ttcactggaa ttccagagca atgggcacga    300
ttactccaaa cttccaacat aacaaaattg gaacagaaga gaacccaca gctgttcta     360 gatgttctca aattctatga ttccaaagaa acagtcaaca accagaaata catgagcttt    420
acatcaggag ataaaagtgc acatggatac atagcagccc atccttcgag tacaaaaaca    480
gcatctgagc ctccattggc ccctcctgtg tctgaagaag aagatgaaga ggaagaagaa    540
gaagaagatg aaaatgagcc accaccagtt atcgcaccaa gaccagagca tacaaaatca    600
atctatactc gttctgtggt tgaatccatt gcttcaccag cagtaccaaa taaagaggtc    660
acaccaccct ctgctgaaaa tgccaattcc agtactttgt acaggaacac agatcggcaa    720
agaaaaaaat ccaagatgac agatgaggag atcttagaga gctaagaag cattgtgagt     780 gttgggggacc caagaaaaa atacacaaga tttgaaaaaa ttggtcaagg ggcatcaggt    840 actgttata cagcactaga cattgcaaca ggacaagagg tggccataaa gcagatgaac     900
cttcaacagc aacccaagaa ggaattaatt attaatgaaa ttctggtcat gagggaaat     960 aagaaccta atattgttaa ttatttagat agctacttgg tgggtgatga actatgggta    1020
gtcatggaat acttggctgg tggctctctg actgatgtgg tcacagagac ctgtatggat    1080
gaaggacaga tagcagctgt ctgcagagag tgcctgcaag ctttggattt cctgcactca    1140
aaccaggtga tccatagaga tataaagagt gacaatattc ttctcgggat ggatggctct    1200
gttaaattga ctgactttgg gttctgtgcc cagatcactc ctgagcaaag taaacgaagc    1260
actatggtgg aaccccata ttggatggca cctgaggtgg tgactcgaaa agcttatggt    1320
ccgaaagttg atatctggtc tcttggaatt atggcaattg aaatggtgga aggtgaaccc    1380
ccttacctta tgaaaatcc actcagggca ttgtatctga tagccactaa tggaactcca    1440
gagctccaga atcctgagag actgtcagct gtattccgtg acttttaaa tcgctgtctt    1500 gagatggatg tggataggcg aggatctgcc aaggagcttt gcagcatcc atttttaaaa    1560 ttagccaagc ctctctccag cctgactcct ctgattatcg ctgcaaagga agcaattaag    1620
```

-continued aacagcagcc gctaa         1635

<210> SEQ ID NO 7
<211> LENGTH: 1776
<212> TYPE: DNA
<213> ORGANISM: Homo sapiens

<400> SEQUENCE: 7

| | | | | | |
|---|---|---|---|---|---|
| atgtttggga | agaggaagaa | gcgggtggag | atctccgcgc | cgtccaactt | cgagcaccgc | 60 |
| gtgcacacgg | gcttcgacca | gcacgagcag | aagttcacgg | ggctgccccg | ccagtggcag | 120 |
| agcctgatcg | aggagtcggc | tcgccggccc | aagcccctcg | tcgacccccgc | ctgcatcacc | 180 |
| tccatccagc | ccggggcccc | caagaccatc | gtgcggggca | gcaaaggtgc | caaagatggg | 240 |
| gccctcacgc | tgctgctgga | cgagtttgag | aacatgtcgg | tgacacgctc | caactccctg | 300 |
| cggagagaca | gcccgccgcc | gcccgcccgt | gcccgccagg | aaaatgggat | gccagaggag | 360 |
| ccggccacca | cggccagagg | gggcccaggg | aaggcaggca | gccgaggccg | gttcgccggt | 420 |
| cacagcgagg | caggtggcgg | cagtggtgac | aggcgacggg | cggggccaga | gaagaggccc | 480 |
| aagtcttcca | gggagggctc | aggggtccc | caggagtcct | cccgggacaa | cgcccccctc | 540 |
| tccgggcctg | atgtcggcac | cccccagcct | gctggtctgg | ccagtggggc | gaaactggca | 600 |
| gctggccggc | cctttaacac | ctacccgagg | gctgacacgg | accacccatc | ccggggtgcc | 660 |
| caggggggagc | ctcatgacgt | ggcccctaac | gggccatcag | cggggggcct | ggccatcccc | 720 |
| cagtcctcct | cctcctcctc | ccggcctccc | acccgagccc | gaggtgcccc | cagccctgga | 780 |
| gtgctgggac | cccacgcctc | agagcccag | ctggcccctc | cagcctgcac | cccgccgcc | 840 |
| cctgctgttc | ctgggccccc | tggccccgc | tcaccacagc | gggagccaca | gcgagtatcc | 900 |
| catgagcagt | tccgggctgc | cctgcagctg | gtggtggacc | caggcgaccc | ccgctcctac | 960 |
| ctggacaact | tcatcaagat | tggcgagggc | tccacgggca | tcgtgtgcat | cgccaccgtg | 1020 |
| cgcagctcgg | gcaagctggt | ggccgtcaag | aagatggacc | tgcgcaagca | gcagaggcgc | 1080 |
| gagctgctct | tcaacgaggt | ggtaatcatg | agggactacc | agcacgagaa | tgtggtggag | 1140 |
| atgtacaaca | gctacctggt | gggggacgag | ctctgggtgg | tcatggagtt | cctggaagga | 1200 |
| ggcgccctca | ccgacatcgt | cacccacacc | aggatgaacg | aggagcagat | cgcagccgtg | 1260 |
| tgccttgcag | tgctgcaggc | cctgtcggtg | ctccacgccc | agggcgtcat | ccaccggac | 1320 |
| atcaagagcg | actcgatcct | gctgacccat | gatggcaggg | tgaagctgtc | agactttggg | 1380 |
| ttctgcgccc | aggtgagcaa | ggaagtgccc | cgaaggaagt | cgctggtcgg | cacgccctac | 1440 |
| tggatggccc | cagagctcat | ctcccgcctt | ccctacgggc | cagaggtaga | catctggtcg | 1500 |
| ctggggataa | tggtgattga | gatggtggac | ggagagcccc | cctacttcaa | cgagccaccc | 1560 |
| ctcaaagcca | tgaagatgat | tcgggacaac | ctgccacccc | gactgaagaa | cctgcacaag | 1620 |
| gtgtcgccat | ccctgaaggg | cttcctggac | cgcctgctgg | tgcgagaccc | tgcccagcgg | 1680 |
| gccacggcag | ccgagctgct | gaagcaccca | ttcctggcca | aggcagggcc | gcctgccagc | 1740 |
| atcgtgcccc | tcatgcgcca | gaaccgcacc | agatga | | | 1776 |

<210> SEQ ID NO 8
<211> LENGTH: 581
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N is any Nucleotide

<400> SEQUENCE: 8

```
gagaccggga acatggcgct gggagcnctg tagcagctga aaggggctg aggcaccgcc      60
gcttcgctga cagccggcca ccagatgttc atgcattcta gagaaagtgg aaaacttaga    120
agcctaatta atgactgtct tctggacctc tgagaccatg tttctagtgt tttccgtgga    180
atattatcag aaatacactg tggtgaaatg cttccacctc ttgctaaaat gaacactgag    240
gaaaatgaa gaagactgac aagcaccagc gaaaagttgc agaatagaaa tagccacact     300
cctctggagt ctttaattca tccacagcca tcatataaag gttttggcat catgtttggg    360
aagaaaaga aaagattga aatatctggc ccgtccaact ttgaacacag ggttcatact      420
gggtttgatc cacaagagca gaagtttacc ggccttcccc agcagtggca cagcctgtta    480
gcagatacgg ccaacaggcc aaagcctatg gtggacccctt catgcatcac acccatccag   540
ctggctccta tgaagacatc gttagaggaa acaaaccctg c                        581
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
gcatcatgtt tgggaagaaa                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10

```
asctcwggkg ccatccarta                                                 20
```

<210> SEQ ID NO 11
<211> LENGTH: 1846
<212> TYPE: DNA
<213> ORGANISM: Homo sapiens

<400> SEQUENCE: 11

```
gcatcatgtt tgggaagaaa aagaaaaaga ttgaaatatc tggcccgtcc aactttgaac     60
acagggttca tactgggttt gatccacaag agcagaagtt taccggcctt ccccagcagt    120
ggcacagcct gttagcagat acggccaaca ggccaaagcc tatggtggac ccttcatgca    180
tcacacccat ccagctggct cctatgaaga caatcgttag aggaaacaaa ccctgcaagg    240
aaacctccat caacgcctg ctagaggatt ttgacaacat ctcggtgact cgctccaact    300
ccctaaggaa agaaagccca cccacccag atcagggagc ctccagccac ggtccaggcc    360
acgcggaaga aaatggcttc atcaccttct cccagtattc cagcgaatcc gatactactg    420
ctgactacac gaccgaaaag tacagggaga gagtctcta tggagatgat ctggatccgt    480
attatagagg cagccacgca gccaagcaaa atgggcacgt aatgaaaatg aagcacgggg    540
aggcctacta ttctgaggtg aagcctttga atccgatttt gccagatttt ctgccgatt    600
atcactcaca tttggactca ctgagcaaac caagtgaata cagtgacctc aagtgggagt    660
atcagagagc ctcgagtagc tcccctctgg attattcatt ccaattcaca ccttctagaa    720
```

```
ctgcagggac cagcgggtgc tccaaggaga gcctggcgta cagtgaaagt gaatggggac    780
ccagcctgga tgactatgac aggaggccaa agtcttcgta cctgaatcag acaagccctc    840
agcccaccat gcggcagagg tccaggtcag gctcgggact ccaggaaccg atgatgccat    900
ttggagcaag tgcatttaaa acccatcccc aaggacactc ctacaactcc tacacctacc    960
ctcgcttgtc cgagcccaca atgtgcattc caaaggtgga ttacgatcga gcacagatgg   1020
tcctcagccc tccactgtca gggtctgaca cctaccccag ggccctgcc  aaactacctc   1080 aaagtcaaag caaatcgggc tattcctcaa gcagtcacca gtaccgtct  gggtaccaca   1140 aagccacctt gtaccatcac ccctccctgc agagcagttc gcagtacatc tccacggctt   1200
cctacctgag ctccctcagc ctctcatcca gcacctaccc gccgcccagc tggggctcct   1260
cctccgacca gcagccctcc agggtgtccc atgaacagtt tcgggcggcc ctgcagctgg   1320
tggtcagccc aggagacccc aggaatact  tggccaactt tatcaaaatc ggggaaggct   1380
caaccggcat cgtatgcatc ggcaccgaga acacacagg  gaaacaagtt gcagtgaaga   1440
aaatggacct ccggaagcaa cagagacgag aactgctttt caatgaggtc gtgatcatgc   1500
gggattacca ccatgacaat gtggttgaca tgtacagcag ctaccttgtc ggcgatgagc   1560
tctgggtggt catggagttt ctagaaggtg gtgccttgac agacattgtg actcacacca   1620
gaatgaatga agaacagata gctactgtct gcctgtcagt tctgagagct ctctcctacc   1680
ttcataacca aggagtgatt cacagggaca taaaaagtga ctccatcctc ctgacaagcg   1740
atggccggat aaagttgtct gattttggtt tctgtgctca agtttccaaa gaggtgccga   1800
agaggaaatc attggttggc actccctact ggatggcccc tgagct              1846

<210> SEQ ID NO 12
<211> LENGTH: 417
<212> TYPE: DNA
<213> ORGANISM: Homo sapiens

<400> SEQUENCE: 12
ataaagttgt ctgattttgg tttctgtgct caagtttcca aagaggtgcc gaagaggaaa     60
tcattggttg gcactcccta ctggatggcc cctgaggtga tttctaggct accttatggg    120
acagaggtgg acatctggtc cctcgggatc atggtgatag aaatgattga tggcgagccc    180
ccctacttca atgagcctcc cctccaggcg atgcggagga tccgggacag tttacctcca    240
agagtgaagg acctacacaa ggtttcttca gtgctccggg gattcctaga cttgatgttg    300
gtgagggagc cctctcagag agcaacagcc caggaactcc tcggacatcc attcttaaaa    360
ctagcaggtc caccgtcttg catcgtcccc ctcatgagac aatacaggca tcactga      417

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gagaccggga acatggcgct                                                 20

<210> SEQ ID NO 14
<211> LENGTH: 22
<212> TYPE: DNA
<213> ORGANISM: Artificial Sequence
<220> FEATURE:
<223> OTHER INFORMATION: Primer
```

```
<400> SEQUENCE: 14
tcagtgatgc ctgtattgtc tc                                              22

<210> SEQ ID NO 15
<211> LENGTH: 8
<212> TYPE: PRT
<213> ORGANISM: Homo sapiens

<400> SEQUENCE: 15

Gly Glu Gly Ser Thr Gly Ile Val
1               5

<210> SEQ ID NO 16
<211> LENGTH: 8
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 16

Gly Xaa Gly Xaa Xaa Gly Xaa Val
1               5

<210> SEQ ID NO 17
<211> LENGTH: 8
<212> TYPE: PRT
<213> ORGANISM: Homo sapiens
<220> FEATURE:
<221> NAME/KEY: misc_feature
<222> LOCATION: (5)..(7)
<223> OTHER INFORMATION: Xaa can be any naturally occurring amino acid

<400> SEQUENCE: 17

His Arg Asp Leu Xaa Xaa Xaa Asn
1               5

<210> SEQ ID NO 18
<211> LENGTH: 8
<212> TYPE: PRT
<213> ORGANISM: Homo sapiens

<400> SEQUENCE: 18

His Arg Asp Ile Lys Ser Asp Ser
1               5

<210> SEQ ID NO 19
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa = Ser or Ala
<220> FEATURE:
```

```
<221> NAME/KEY: misc_feature
<222> LOCATION: (5)..(5)
<223> OTHER INFORMATION: Xaa can be any naturally occurring amino acid

<400> SEQUENCE: 19

Asp Xaa Trp Xaa Xaa Gly
1               5

<210> SEQ ID NO 20
<211> LENGTH: 6
<212> TYPE: PRT
<213> ORGANISM: Homo sapiens

<400> SEQUENCE: 20

Asp Ile Trp Ser Leu Gly
1               5
```